US007662548B2

(12) United States Patent
Gray et al.

(10) Patent No.: US 7,662,548 B2
(45) Date of Patent: Feb. 16, 2010

(54) METHOD OF SCREENING FOR MODULATORS OF HIV INFECTION

(75) Inventors: Patrick W. Gray, Seattle, WA (US); Vicki L. Schweickart, Seattle, WA (US); Carol J. Raport, Bothell, WA (US)

(73) Assignee: Euroscreen S.A. ICOS Corporation, Brussels (BE)

( * ) Notice: Subject to any disclaimer, the term of this patent is extended or adjusted under 35 U.S.C. 154(b) by 418 days.

(21) Appl. No.: 11/068,686

(22) Filed: Feb. 28, 2005

(65) Prior Publication Data
US 2005/0260565 A1 Nov. 24, 2005

Related U.S. Application Data

(63) Continuation of application No. 10/106,623, filed on Mar. 26, 2002, now abandoned, which is a continuation of application No. 08/771,276, filed on Dec. 20, 1996, now Pat. No. 6,797,811, which is a continuation-in-part of application No. 08/661,393, filed on Jun. 7, 1996, now Pat. No. 6,268,477, which is a continuation-in-part of application No. 08/575,967, filed on Dec. 20, 1995, now Pat. No. 6,265,184.

(51) Int. Cl.
*C12Q 1/70* (2006.01)
(52) U.S. Cl. ........................... 435/5; 530/350
(58) Field of Classification Search ........................ None
See application file for complete search history.

(56) References Cited

U.S. PATENT DOCUMENTS

| 4,886,742 | A  | 12/1989 | Kortright et al. |
| 4,888,920 | A  | 12/1989 | Marulic |
| 5,215,915 | A  | 6/1993  | Tiberi et al. |
| 6,025,154 | A  | 2/2000  | Li et al. |
| 6,265,184 | B1 | 7/2001  | Gray et al. |
| 6,268,477 | B1 | 7/2001  | Gray et al. |

FOREIGN PATENT DOCUMENTS

| AU | A 50202/96 | 8/1996 |
| EP | 96870021.1 | 3/1996 |
| EP | 96870102.9 | 8/1996 |
| JP | 10-510719 | 10/1998 |
| JP | 10-512753 | 12/1998 |
| JP | 11-502420 | 3/1999 |
| WO | WO 96/22371 | 7/1996 |
| WO | WO 96/39437 | 12/1996 |
| WO | WO 97/21812 | 6/1997 |
| WO | WO 97/22698 | 6/1997 |
| WO | WO 97/26009 | 7/1997 |
| WO | WO 97/32019 | 9/1997 |
| WO | WO 97/44055 | 11/1997 |
| WO | WO 97/45543 | 12/1997 |
| WO | WO 97/47318 | 12/1997 |
| WO | WO 97/47319 | 12/1997 |

OTHER PUBLICATIONS

Combadiere et al. Cloning and functional expression of human eosinophil CC chemokine receptor. The Journal of Biological Chemistry, Jul. 14, 1995, vol. 270, No. 27, 16491-16494.*
Combadiere et al. Additions and corrections to cloning and functional expression of human eosinophil CC chemokine receptor. The Journal of Biological Chemistry, Dec. 15, 1995, vol. 270, No. 50, 30235C-30235.*
Search result No. 1 for SEQ ID No. 2 from the rup database.*
Ahuja and Murphy, "Chemokine Receptors and Molecular Mimicry," *Immunol. Today*, 15(6):281 (1994).
Ahuja et al., "Molecular Evolution of the Human Interleukin-8 Receptor Gene Cluster," *Nature Genetics*, 2:31-36 (1992).
Ahuja et al., "Molecular Piracy of Mammalian Interleukin-8 Receptor Type B by Herpesvirus Saimiri," *J. Biol. Chem.*, 268 (28):20691-20694 (1993).
Alkhatib et al., "CC CKR5: A RANTES, MIP-1α, MIP-1β Receptor as a Fusion Cofactor for Macrophage-Tropic HIV-1," *Science*, 272:1955-1958 (1996).
Baggiolini et al., "Interleukin-8 and related Chemotactic Cytokines CXC and CC Chemokines," *Advances in Immunol.*, 55:97-179 (1994).
Bartz et al., "Human Immunodeficiency Virus Type 1 Cell Cycle Control: Vpr is Cytostatic and Mediates $G_2$ Accumulationby a Mechanism Which Differs from DNA Damage Checkpoint Control," *J. Virol.*, 70:2324-2331 (1996).
Broaddus et al., "Neutralization of IL-8 Inhibits Neutrophil Influx in a Rabbit Model of Endotoxin-Induced Pleurisy," *J. of Immunol.*, 152:2960-2967 (1994).
Cacalano et al., "Neutrophil and B Cell Expansion in Mice that Lack the Murine II-8 Receptor Homolog," *Science*, 265:682-684 (1994).
Capecchi, "Altering the Genome by Homologous Recombination," *Science* 244:1288-1292 (1989).
Chackerian et al., "Characterization of a CD4-Expressing Macaque Cell Line That Can Detect Virus after a Single Replication Cycle and Can Be Infected by Diverse Simian Immunodeficency Virus Isolates," *Virology*, 213(2):6499-6505 (1995).

(Continued)

*Primary Examiner*—Emily M. Le
(74) *Attorney, Agent, or Firm*—Kathleen Williams; Amy DeCloux; Gabriel J. McCool

(57) ABSTRACT

The present invention provides polynucleotides that encode the chemokine receptors 88-2B or 88C and materials and methods for the recombinant production of these two chemokine receptors. Also provided are assays utilizing the polynucleotides which facilitate the identification of ligands and modulators of the chemokine receptors. Receptor fragments, ligands, modulators, and antibodies are useful in the detection and treatment of disease states associated with the chemokine receptors such as atherosclerosis, rheumatoid arthritis, tumor growth suppression, asthma, viral infection, AIDS, and other inflammatory conditions.

10 Claims, No Drawings

OTHER PUBLICATIONS

Charo et al., "Molecular Cloning and Functional Expression of Two Monocyte Chemoattractant protein 1 Receptors Reveals Alternative Splicing of the Carboxyl-Terminal Tails," *Proc Natl. Acad. Sci., USA*, 91:2752-2756 (1994).

Chen et al., "CCR3 and CCR5 are co-receptors for HIV-1 infection of microglia," Nature, vol. 385, No. 6617, pp. 645-649 (1997).

Clapham et al., "Specific Cell Surface Requirements for the Infection of CD4-Positive Cells by Human Immunodeficency Virus Types 1 and 2 and by Simian Immunodeficency Virus", *Virol.*, 181:703-715 (1991).

Clapham et al., "Human Immunodeficency Virus Type 2 Infection and Fusion of CD4-Negative Human Cell Lines: Induction and Enhancement by Soluble CD4," *J. Virol.*, 66:3531-3537 (1992).

Cocchi et al., "Identification of RANTES, MIP-1α, and MIP-1β as the Major HIV-Suppressive Factors Produced by CD8+ T Cells," *Science*, 270:1811-1815 (1995).

Combadiere et al., "Cloning and Functional Expression of a Human Eosinophil CC Chemokine," *J. Biol. Chem.* 270(27):16491-16494 and p. 11034 (1995).

Combadiere et al., "Cloning and Functional Expression of a Human Eosinophil CC Chemokine," *J. Biol. Chem.* 271(18): 11304 (1996).

Conklin et al., "Substitution of Three Amino Acids Switches Receptor Specificity of $G_q\alpha$ to that of $G_i\alpha$," Nature 363:274-276 (1993).

Cundell et al., "*Streptococcus Pneumonia* Anchor to Activated Human Cells by the Receptor for Platelet-activating Factor," *Nature* 377:435-438 (1995).

Deng et al., "Identification of a Major Co-receptor for Primary Isolates of HIV-1," *Nature*, 381:661-666 (1996).

Dewhurst et al., "Sequence Analysis and Acute Pathogenicity of Molecularly Cloned $SIV_{SMM-PBJ14}$," *Nature*, 345:636-640 (1990).

Dragic et al., "HIV-1 Entry into $CD4^+$ Cells is Mediated by the Chemokine Receptor CC-CKR-5," *Nature* 381:667-673 (1996).

Endres et al., "CD4-Independent Infection by HIV-2 is Mediated by Fusio/CXCR4," *Cell*, 87(4):745-756 (1996).

Ernst et al., "Biochemical and Biologic Characterization of Murine Monocyte Chemoattractant Protein-1," *J. Immunol* 152:3541-3549 (1994).

Feng et al., "HIV-1 Entry Cofactor: Functional cDNA Cloning of a Seven-Transmembrane, G Protein-Coupled Receptor," *Science* 272:872-877 (1996).

Gao et al., "Genetic Diversity of Human Immunodeficiency Virus Type 2: Evidence for Distinct Sequence Subtypes with Differences in Virus Biology," *J. Virol*, 68(11):7433-7447 (1992).

Harrington and Geballe, "Cofactor Requirement for Human Immunodeficiency Virus Type 1 Entry into a CD4-Expressing Human Cell Line," *J. Virol*, 67:5939-5947 (1993).

Harlow et al., In: *Antibodies, A Laboratory Manual*, Chapter 5, p. 76, Cold Spring Harbor Laboratory (1988).

Holmes et al., "Structure and Functional Expression of a Human Interleukin-8 Receptor," *Science*, 253:1278-1280 (1991).

Horuk et al., "A Receptor for the Malarial Parasite *Plasmodium vivax*: The Erythrocyte Chemokine Receptor," *Science*, 261:1182-1184 (1993).

Hung et al., "Thrombin-Induced Events in Non-Platelet Cells Are Mediated by the Unique Proteolytic Mechanism Established for the Cloned Platelet Thrombin Receptor," *J. Cell Biol.*, 116(3):827-832 (1992).

Harrington and Geballe, "Cofactor Requirement for Human Immunodeficiency Virus Type 1 Entry into a CD4-Expressing Human Cell Line," *J. Virol*, 67:5939-5947 (1993).

Holmes et al., "Structure and Functional Expression of a Human Interleukin-8 Receptor," *Science*, 253:1278-1280 (1991).

Horuk et al., "A Receptor for the Malarial Parasite *Plasmodium vivax*: The Erythrocyte Chemokine Receptor," *Science*, 261:1182-1184 (1993).

Hung et al., "Thrombin-Induced Events in Non-Platelet Cells Are Mediated by the Unique Proteolytic Mechanism Established for the Cloned Platelet Thrombin Receptor," *J. Cell Biol.*, 116(3):827-832 (1992).

Ishi et al., "Determinants of Thrombin Receptor Cleavage, Receptor Domains Involved, Specificity, and Role of the P3 Aspartate," *J. Biol. Chem.* 270(27):16435-16440 (1995).

Kimpton and Emerman, "Detection of Replication-Competent and Pseudotyped Human Immunodeficiency Virus with a Sensitive Cell Line on the Basis of Activation of an Integrated β-Galactosidase Gene," *J. Virol.* 66(4):2232-2239 (1992).

Kitaura et al., "Molecular Cloning of Human Eotaxin, an Eosinophil-selective CC Chemokine, and Identification of a Specific Eosinophil Eotaxin Receptor, CC Chemokine Receptor 3," *J. Biol. Chem.*, 271(13):7725-7730 (1996).

Lee et al., "Characterization of Two High Affinity Human Interleukin-8 Receptors", *J. Biol. Chem.*, 267(23):16283-16287 (1992).

Lehner et al., "Protective Mucosal Immunity Elicted by Targeted Iliac Lymph Node Immunization with a Subunit SIV Envelope and Core Vaccine in Macaques," *Nature Medicine*, 2:767 (1996).

Leong et al., "Complete Mutagenesis of the Extracellular Domain of Interleukin-8 (IL-8) Type A Receptor Identifies Charged Residues Mediating Il-8 Binding and Signal Transduction", *J. Biol. Chem.*, 269(30):19343-19348 (1994).

Lerner, "Tapping the immunological repertoire to produce antibodies of predetermined specificity," Nature, 299:592-596 (1982).

Lewin, "Receptors and Signal Transduction: Channels and Ion Uptake," *GENES V*, Chapter 12, pp. 319-348 (1994).

Linder and Gilman, "G Proteins," *Sci. Am.*, 267:56-65 (1992).

Morgenstern and Land, "Advanced Mammalian Gene Transfer: High Titre Retroviral Vectors with Multiple Drug Selection Markers and a Complementary Helper-Free Packaging Cell Line," *Nucleic Acids Research*, 18(12):3587-3596 (1990).

Murphy, "The Molecular Biology of Leukocyte Chemoattractant Receptors," *Ann. Rev. Immunol.*, 12:593-633 (1994).

Murphy and Tiffany, "Cloning of the Complimentary DNA Encoding a Functional Human Interleukin-8 Receptor," *Science*, 253:1280-1283 (1991).

Neote et al., "Molecular Cloning, Functional Expression, and Signaling Characteristics of a C-C Chemokine Receptor," *Cell*, 72:415-425 (1993).

Nussbaum et al., "Fusogenic Mechanisms of Enveloped-Virus Glycoproteins Analyzed by a Novel Recombinant Vaccinia Virus-Based Assay Quantitating Cell Fusion-Dependent Reporter Gene Activation," *J. Virol* 68:5411(1994).

Oppenheim et al., "Properties of the Novel Proinflammatory Supergene "Intercrine" Cytokine Family," *Ann. Rev. Immunol.* 9:617-648 (1991).

Probst et al., "Review Article: Sequence Alignment of the G-Protein Coupled Receptor Superfamily," *DNA and Cell Biology* 11(1):1-20 (1992).

Raport et al., "The Orphan G Protein-Coupled Receptor-Encoding Gene V28 is Closely Related to Genes for Chemokine Receptors and is Expressed in Lymphoid and Neural Tissues," *Gene*, 163:295-299 (1995).

Rhame, F., "Acquired Immunodeficiency Syndrome," *Infectious Diseases* 5:628-652 (1994).

Sambrook et al., §§9.47-9.51 in Molecular CLoning: A Laboratory Manual, Cold Spring Harbor Laboratory Press, Cold Spring Harbor, New York (1989).

Samson et al., "Molecular Cloning and Functional Expression of a New Human CC-Chemokine Receptor Gene," *Biochemistry* 35:3362-3367 (1996).

Schall and Bacon, "Chemokines, Leukocyte Trafficking, and Inflammation," *Curr. Opin. Immunol.* 6:865-873 (1994).

Sevier et al., "Monoclonal Antibodies in Clinical Immunology," *Clin. Chem.*, 27(11):1797-1806 (1981).

Springer, "Traffic Signals for Lymphocyte Recirculation and Leukocyte Emigration: The Multistep Paradigm", *Cell*, 76:301-314 (1994).

Tjoelker et al., "Anti-Inflammatory Properties of a Platelet-Activating Factor Acetylhydrolase", *Nature*, 374:549-553 (1995).

Trkola et al., "CD4-Dependent, Antibody-Sensitive Interactions Between HIV-1 and its Co-Receptor CCR-5," *Nature*, 384(6605):184-187 (1996).

Wu et al., "CD4-Induced Interaction of Primary HIV-1 gp120 Glycoproteins with the Chemokine Receptor CCR-5," *Nature*, 384:179-183 (1996).

* cited by examiner

METHOD OF SCREENING FOR MODULATORS OF HIV INFECTION

This is a continuation application of U.S. patent application Ser. No. 10/106,623 filed Mar. 26, 2002, which is a continuation of U.S. patent application Ser. No. 08/771,276 filed Dec. 20, 1996, which is a continuation-in-part of U.S. patent application Ser. No. 08/661,393 filed Jun. 7, 1996 (issued as U.S. Pat. No. 6,268,477 on Jul. 31, 2001), which was in turn a continuation-in-part of U.S. patent application Ser. No. 08/575,967 filed Dec. 20, 1995 (issued as U.S. Pat. No. 6,265,184 on Jul. 24, 2001). All of these priority applications are incorporated by reference in their entirety.

FIELD OF THE INVENTION

The present invention relates generally to signal transduction pathways. More particularly, the present invention relates to chemokine receptors, nucleic acids encoding chemokine receptors, chemokine receptor ligands, modulators of chemokine receptor activity, antibodies recognizing chemokines and chemokine receptors, methods for identifying chemokine receptor ligands and modulators, methods for producing chemokine receptors, and methods for producing antibodies recognizing chemokine receptors.

BACKGROUND OF THE INVENTION

Recent advances in molecular biology have led to an appreciation of the central role of signal transduction pathways in biological processes. These pathways comprise a central means by which individual cells in a multicellular organism communicate, thereby coordinating biological processes. See Springer, *Cell* 76:301-314 (1994), Table I, for a model. One branch of signal transduction pathways, defined by the intracellular participation of guanine nucleotide binding proteins (G-proteins), affects a broad range of biological processes.

Lewin, *GENES* V 319-348 (1994) generally discusses G-protein signal transduction pathways which involve, at a minimum, the following components: an extracellular signal (e.g., neurotransmitters, peptide hormones, organic molecules, light, or odorants), a signal-recognizing receptor [G-protein-coupled receptor, reviewed in Probst et al., *DNA and Cell Biology* 11:1-20 (1992) and also known as GPR or GPCR], and an intracellular, heterotrimeric GTP-binding protein, or G protein. In particular, these pathways have attracted interest because of their role in regulating white blood cell or leukocyte trafficking.

Leukocytes comprise a group of mobile blood cell types including granulocytes (i.e., neutrophils, basophils, and eosinophils), lymphocytes, and monocytes. When mobilized and activated, these cells are primarily involved in the body's defense against foreign matter. This task is complicated by the diversity of normal and pathological processes in which leukocytes participate. For example, leukocytes function in the normal inflammatory response to infection. Leukocytes are also involved in a variety of pathological inflammations. For a summary, see Schall et al., *Curr. Opin. Immunol.* 6:865-873 (1994). Moreover, each of these processes can involve unique contributions, in degree, kind, and duration, from each of the leukocyte cell types.

In studying these immune reactions, researchers initially concentrated on the signals acting upon leukocytes, reasoning that a signal would be required to elicit any form of response. Murphy, *Ann. Rev. Immunol.* 12:593-633 (1994) has reviewed members of an important group of leukocyte signals, the peptide signals. One type of peptide signal comprises the chemokines (chemoattractant cytokines), termed intercrines in Oppenheim et al., *Ann. Rev. Immunol.* 9:617-648 (1991). In addition to Oppenheim et al., Baggiolini et al., *Advances in Immunol.* 55:97-179 (1994), documents the growing number of chemokines that have been identified and subjected to genetic and biochemical analyses.

Comparisons of the amino acid sequences of the known chemokines have led to a classification scheme which divides chemokines into two groups: the α group characterized by a single amino acid separating the first two cysteines (CXC; N-terminus as referent), and the β group, where these cysteines are adjacent (CC). See Baggiolini et al., supra. Correlations have been found between the chemokines and the particular leukocyte cell types responding to those signals. Schall et al., supra, has reported that the CXC chemokines generally affect neutrophils; the CC chemokines tend to affect monocytes, lymphocytes, basophils and eosinophils. For example, Baggiolini et al., supra, recited that RANTES, a CC chemokine, functions as a chemoattractant for monocytes, lymphocytes (i.e., memory T cells), basophils, and eosinophils, but not for neutrophils, while inducing the release of histamine from basophils.

Chemokines were recently shown by Cocchi et. al., *Science*, 270: 1811-1815 (1995) to be suppressors of HIV proliferation. Cocchi et al. (supra) demonstrated that RANTES, MIP-1α, and MIP-1β suppressed HIV-1, HIV-2 and SIV infection of a $CD4^+$ cell line designated PM1 and of primary human peripheral blood mononuclear cells.

Recently, however, attention has turned to the cellular receptors that bind the chemokines, because the extracellular chemokines seem to contact cells indiscriminately, and therefore lack the specificity needed to regulate the individual leukocyte cell types.

Murphy (supra) reported that the GPCR superfamily of receptors includes the chemokine receptor family. The typical chemokine receptor structure includes an extracellular chemokine-binding domain located near the N-terminus, followed by seven spaced regions of predominantly hydrophobic amino acids capable of forming membrane-spanning α-helices. Between each of the α-helical domains are hydrophilic domains localized, alternately, in the intra- or extracellular spaces. These features impart a serpentine conformation to the membrane-embedded chemokine receptor. The third intracellular loop typically interacts with G-proteins. In addition, Murphy (supra) noted that the intracellular carboxyl terminus is also capable of interacting with G-proteins.

The first chemokine receptors to be analyzed by molecular cloning techniques were the two neutrophil receptors for human IL8, a CXC chemokine. Holmes et al., *Science* 253: 178-1280 (1991) and Murphy et al., *Science* 253:1280-1283 (1991), reported the cloning of these two receptors for IL8. Lee et al., *J. Biol. Chem.* 267:16283-16287 (1992), analyzed the cDNAs encoding these receptors and found 77% amino acid identity between the encoded receptors, with each receptor exhibiting features of the G protein coupled receptor family. One of these receptors is specific for IL-8, while the other binds and signals in response to IL-8, gro/MGSA, and NAP-2. Genetic manipulation of the genes encoding IL-8 receptors has contributed to our understanding of the biological roles occupied by these receptors. For example, Cacalano et al., *Science* 265:682-684 (1994) reported that deletion of the IL-8 receptor homolog in the mouse resulted in a pleiotropic phenotype involving lymphadenopathy and splenomegaly. In addition, a study of missense mutations described in Leong et al., *J. Biol. Chem.* 269:19343-19348 (1994) revealed amino acids in the IL-8 receptor that were critical for IL-8 binding.

Domain swapping experiments discussed in Murphy (supra) implicated the amino terminal extracellular domain as a determinant of binding specificity.

Several receptors for CC chemokines have also been identified and cloned. CCCKR1 binds both MIP-1α and RANTES and causes intracellular calcium ion flux in response to both ligands. Charo et al., *Proc Natl. Acad. Sci.* (*USA*) 91:2752-2756 (1994) reported that another CC chemokine receptor, MCP-R1 (CCCKR2), is encoded by a single gene that produces two splice variants which differ in their carboxyl terminal domains. This receptor binds and responds to MCP-3 in addition to MCP-1.

A promiscuous receptor that binds both CXC and CC chemokines has also been identified. This receptor was originally identified on red blood cells and Horuk et al., *Science* 261:1182-1184 (1993) reports that it binds IL-8, NAP-2, GROα, RANTES, and MCP-1. The erythrocyte chemokine receptor shares about 25% identity with other chemokine receptors and may help to regulate circulating levels of chemokines or aid in the presentation of chemokines to their targets. In addition to binding chemokines, the erythrocyte chemokine receptor has also been shown to be the receptor for plasmodium vivax, a major cause of malaria (id.) Another G-protein coupled receptor which is closely related to chemokine receptors, the platelet activating factor receptor, has also been shown to be the receptor for a human pathogen, the bacterium *Streptococcus pneumoniae* [Cundell et al., *Nature* 377:435-438 (1995)].

In addition to the mammalian chemokine receptors, two viral chemokine receptor homologs have been identified. Ahuja et al., *J. Biol. Chem.* 268:20691-20694 (1993) describes a gene product from Herpesvirus saimiri that shares about 30% identity with the IL-8 receptors and binds CXC chemokines. Neote et al., *Cell*, 72:415-425 (1993) reports that human cytomegalovirus contains a gene encoding a receptor sharing about 30% identity with the CC chemokine receptors which binds MIP-1α, MIP-1β, MCP-1, and RANTES. These viral receptors may affect the normal role of chemokines and provide a selective pathological advantage for the virus.

Because of the broad diversity of chemokines and their activities, there are numerous receptors for the chemokines. The receptors which have been characterized represent only a fraction of the total complement of chemokine receptors. There thus remains a need in the art for the identification of additional chemokine receptors. The availability of these novel receptors will provide tools for the development of therapeutic modulators of chemokine or chemokine receptor function. It is contemplated by the present invention that such modulators are useful as therapeutics for the treatment of atherosclerosis, rheumatoid arthritis, tumor growth suppression, asthma, viral infections, and other inflammatory conditions. Alternatively, fragments or variants of the chemokine receptors, or antibodies recognizing those receptors, are contemplated as therapeutics.

SUMMARY OF THE INVENTION

The present invention provides purified and isolated nucleic acids encoding chemokine receptors involved in leukocyte trafficking. Polynucleotides of the invention (both sense and anti-sense strands thereof) include genomic DNAs, cDNAs, and RNAs, as well as completely or partially synthetic nucleic acids. Preferred polynucleotides of the invention include the DNA encoding the chemokine receptor 88-2B that is set out in SEQ ID NO:3, the DNA encoding the chemokine receptor 88C that is set out in SEQ ID NO:1, and DNAs which hybridize to those DNAs under standard stringent hybridization conditions, or which would hybridize but for the redundancy of the genetic code. Exemplary stringent hybridization conditions are as follows: hybridization at 42° C. in 50% formamide, 5×SSC, 20 mM sodium phosphate, pH 6.8 and washing in 0.2×SSC at 55° C. It is understood by those of skill in the art that variation in these conditions occurs based on the length and GC nucleotide content of the sequences to be hybridized. Formulas standard in the art are appropriate for determining exact hybridization conditions. See Sambrook et al., §§ 9.47-9.51 in Molecular Cloning: A Laboratory Manual, Cold Spring Harbor Laboratory Press, Cold Spring Harbor, N.Y. (1989). Also contemplated by the invention are polynucleotides encoding domains of 88-2B or 88C, for example, polynucleotides encoding one or more extracellular domains of either protein or other biologically active fragments thereof. 88-2B extracellular domains correspond to SEQ ID NO:3 and SEQ ID NO:4 at amino acid residues 1-36, 93-107, 171-196, and 263-284. The extracellular domains of 88-2B are encoded by polynucleotide sequences corresponding to SEQ ID NO:3 at nucleotides 362-469, 638-682, 872-949, and 1148-1213. Extracellular domains of 88C correspond to SEQ ID NO:1 and SEQ ID NO:2 at amino acid residues 1-32, 89-112, 166-191, and 259-280. The 88C extracellular domains are encoded by polynucleotide sequences that correspond to SEQ ID NO:1 at nucleotides 55-150, 319-390, 550-627, and 829-894. The invention also comprehends polynucleotides encoding intracellular domains of these chemokine receptors. The intracellular domains of 88-2B include amino acids 60-71, 131-151, 219-240, and 306-355 of SEQ ID NO:3 and SEQ ID NO:4. Those domains are encoded by polynucleotide sequences corresponding to SEQ ID NO:3 at nucleotides 539-574, 752-814, 1016-1081, and 1277-1426, respectively. The 88C intracellular domains include amino acid residues 56-67, 125-145, 213-235, and 301-352 of SEQ ID NO:1 and SEQ ID NO:2. The intracellular domains of 88C are encoded by polynucleotide sequences corresponding to SEQ ID NO:1 at nucleotides 220-255, 427-489, 691-759, and 955-1110. Peptides corresponding to one or more of the extracellular or intracellular domains, or antibodies raised against those peptides, are contemplated as modulators of receptor activities, especially ligand and G protein binding activities of the receptors.

The nucleotide sequences of the invention may also be used to design oligonucleotides for use as labeled probes to isolate genomic DNAs encoding 88-2B or 88C under stringent hybridization conditions (i.e., by Southern analyses and polymerase chain reaction methodologies). Moreover, these oligonucleotide probes can be used to detect particular alleles of the genes encoding 88-2B or 88C, facilitating both diagnosis and gene therapy treatments of disease states associated with particular alleles. In addition, these oligonucleotides can be used to alter chemokine receptor genetics to facilitate identification of chemokine receptor modulators. Also, the nucleotide sequences can be used to design antisense genetic elements of use in exploring or altering the genetics and expression of 88-2B or 88C. The invention also comprehends biological replicas (i.e., copies of isolated DNAs made in vivo or in vitro) and RNA transcripts of DNAs of the invention. Autonomously replicating recombinant constructions such as plasmid, viral, and chromosomal (e.g., YAC) nucleic acid vectors effectively incorporating 88-2B or 88C polynucleotides, and, particularly, vectors wherein DNA effectively encoding 88-2B or 88C is operatively linked to one or more endogenous or heterologous expression control sequences are also provided.

The 88-2B and 88C receptors may be produced naturally, recombinantly or synthetically. Host cells (prokaryotic or eukaryotic) transformed or transfected with polynucleotides of the invention by standard methods may be used to express the 88-2B and 88C chemokine receptors. Beyond the intact 88-2B or 88C gene products, biologically active fragments of 88-2B or 88C, analogs of 88-2B or 88C, and synthetic peptides derived from the amino acid sequences of 88-2B, set out in SEQ ID NO:4, or 88C, set out in SEQ ID NO:2, are contemplated by the invention. Moreover, the 88-2B or 88C gene product, or a biologically active fragment of either gene product, when produced in a eukaryotic cell, may be post-translationally modified (e.g., via disulfide bond formation, glycosylation, phosphorylation, myristoylation, palmitoylation, acetylation, etc.) The invention further contemplates the 88-2B and 88C gene products, or biologically active fragments thereof, in monomeric, homomultimeric, or heteromultimeric conformations.

In particular, one aspect of the invention involves antibody products capable of specifically binding to the 88-2B or 88C chemokine receptors. The antibody products are generated by methods standard in the art using recombinant 88-2B or 88C receptors, synthetic peptides or peptide fragments of 88-2B or 88C receptors, host cells expressing 88-2B or 88C on their surfaces, or 88-2B or 88C receptors purified from natural sources as immunogens. The antibody products may include monoclonal antibodies or polyclonal antibodies of any source or sub-type. Moreover, monomeric, homomultimeric, and heteromultimeric antibodies, and fragments thereof, are contemplated by the invention. Further, the invention comprehends CDR-grafted antibodies, "humanized" antibodies, and other modified antibody products retaining the ability to specifically bind a chemokine receptor.

The invention also contemplates the use of antibody products for detection of the 88-2B or 88C gene products, their analogs, or biologically active fragments thereof. For example, antibody products may be used in diagnostic procedures designed to reveal correlations between the expression of 88-2B, or 88C, and various normal or pathological states. In addition, antibody products can be used to diagnose tissue-specific variations in expression of 88-2B or 88C, their analogs, or biologically active fragments thereof. Antibody products specific for the 88-2B and 88C chemokine receptors may also act as modulators of receptor activities. In another aspect, antibodies to 88-2B or 88C receptors are useful for therapeutic purposes.

Assays for ligands capable of interacting with the chemokine receptors of the invention are also provided. These assays may involve direct detection of chemokine receptor activity, for example, by monitoring the binding of a labeled ligand to the receptor. In addition, these assays may be used to indirectly assess ligand interaction with the chemokine receptor. As used herein the term "ligand" comprises molecules which are agonists and antagonists of 88-2B or 88C, and other molecules which bind to the receptors.

Direct detection of ligand binding to a chemokine receptor may be achieved using the following assay. Test compounds (i.e., putative ligands) are detectably labeled (e.g., radioiodinated). The detectably labeled test compounds are then contacted with membrane preparations containing a chemokine receptor of the invention. Preferably, the membranes are prepared from host cells expressing chemokine receptors of the invention from recombinant vectors. Following an incubation period to facilitate contact between the membrane-embedded chemokine receptors and the detectably labeled test compounds, the membrane material is collected on filters using vacuum filtration. The detectable label associated with the filters is then quantitated. For example, radiolabels are quantitated using liquid scintillation spectrophotometry. Using this technique, ligands binding to chemokine receptors are identified. To confirm the identification of a ligand, a detectably labeled test compound is exposed to a membrane preparation displaying a chemokine receptor in the presence of increasing quantities of the test compound in an unlabeled state. A progressive reduction in the level of filter-associated label as one adds increasing quantities of unlabeled test compound confirms the identification of that ligand.

Agonists are ligands which bind to the receptor and elicit intracellular signal transduction and antagonists are ligands which bind to the receptor but do not elicit intracellular signal transduction. The determination of whether a particular ligand is an agonist or an antagonist can be determined, for example, by assaying G protein-coupled signal transduction pathways. Activation of these pathways can be determined by measuring intracellular $ca^{++}$ flux, phospholipase C activity or adenylyl cyclase activity, in addition to other assays (see examples 5 and 6).

As discussed in detail in the Examples herein, chemokines that bind to the 88C receptor include RANTES, MIP-1α, and MIP-1β, and chemokines that bind to the 88-2B receptor include RANTES.

In another aspect, modulators of the interaction between the 88C and 88-2B receptors and their ligands are specifically contemplated by the invention. Modulators of chemokine receptor function may be identified using assays similar to those used for identifying ligands. The membrane preparation displaying a chemokine receptor is exposed to a constant and known quantity of a detectably labeled functional ligand. In addition, the membrane-bound chemokine receptor is also exposed to an increasing quantity of a test compound suspected of modulating the activity of that chemokine receptor. If the levels of filter-associated label correlate with the quantity of test compound, that compound is a modulator of the activity of the chemokine receptor. If the level of filter-associated label increases with increasing quantities of the test compound, an activator has been identified. In contrast, if the level of filter-associated label varies inversely with the quantity of test compound, an inhibitor of chemokine receptor activity has been identified. Testing for modulators of receptor binding in this way allows for the rapid screening of many putative modulators, as pools containing many potential modulators can be tested simultaneously in the same reaction.

The indirect assays for receptor binding involve measurements of the concentration or level of activity of any of the components found in the relevant signal transduction pathway. Chemokine receptor activation often is associated with an intracellular $Ca^{++}$ flux. Cells expressing chemokine receptors may be loaded with a calcium-sensitive dye. Upon activation of the expressed receptor, a $Ca^{++}$ flux would be rendered spectrophotometrically detectable by the dye. Alternatively, the $Ca^{++}$ flux could be detected microscopically. Parallel assays, using either technique, may be performed in the presence and absence of putative ligands. For example, using the microscopic assay for $Ca^{++}$ flux, RANTES, a CC chemokine, was identified as a ligand of the 88-2B chemokine receptor. Those skilled in the art will recognize that these assays are also useful for identifying and monitoring the purification of modulators of receptor activity. Receptor activators and inhibitors will activate or inhibit, respectively, the interaction of the receptors with their ligands in these assays.

Alternatively, the association of chemokine receptors with G proteins affords the opportunity of assessing receptor activity by monitoring G protein activities. A characteristic activity of G proteins, GTP hydrolysis, may be monitored using, for example, $^{32}$P-labeled GTP.

G proteins also affect a variety of other molecules through their participation in signal transduction pathways. For example, G protein effector molecules include adenylyl cyclase, phospholipase C, ion channels, and phosphodiesterases. Assays focused on any of these effectors may be used to monitor chemokine receptor activity induced by ligand binding in a host cell that is both expressing the chemokine receptor of interest and contacted with an appropriate ligand. For example, one method by which the activity of chemokine receptors may be detected involves measuring phospholipase C activity. In this assay, the production of radiolabeled inositol phosphates by host cells expressing a chemokine receptor in the presence of an agonist is detected. The detection of phospholipase activity may require cotransfection with DNA encoding an exogenous G protein. When cotransfection is required, this assay can be performed by cotransfection of chimeric G protein DNA, for example, Gqi5 [Conklin et al., Nature 363:274-276 (1993)], with 88-2B or 88C DNA and detecting phosphoinositol production when the cotransfected cell is exposed to an agonist of the 88-2B or 88C receptor. Those skilled in the art will recognize that assays focused on G-protein effector molecules are also useful for identifying and monitoring the purification of modulators of receptor activity. Receptor activators and inhibitors will activate or inhibit, respectively, the interaction of the receptors with their ligands in these assays.

Chemokines have been linked to many inflammatory diseases, such as psoriasis, arthritis, pulmonary fibrosis and atherosclerosis. See Baggiolini et al. (supra). Inhibitors of chemokine action may be useful in treating these conditions. In one example, Broaddus et al., J. of Immunol. 152:2960-2967 (1994), describes an antibody to IL-8 which can inhibit neutrophil recruitment in endotoxin-induced pleurisy, a model of acute inflammation in rabbit lung. It is also contemplated that ligand or modulator binding to, or the activation of, the 88C receptor may be useful in treatment of HIV infection and HIV related disease states. Modulators of chemokine binding to specific receptors contemplated by the invention may include antibodies directed toward a chemokine or a receptor, biological or chemical small molecules, or synthetic peptides corresponding to fragments of the chemokine or receptor.

Administration of compositions containing 88-2B or 88C modulators to mammalian subjects, for the purpose of monitoring or remediating normal or pathological immune reactions And viral infections including infection by retroviruses such as HIV-1, HIV-2 and SIV is contemplated by the invention. In particular, the invention comprehends the mitigation of inflammatory responses, abnormal hematopoietic processes, and viral infections by delivery of a pharmaceutically acceptable quantity of 88-2B or 88C chemokine receptor modulators. The invention further comprehends delivery of these active substances in pharmaceutically acceptable compositions comprising carriers, diluents, or medicaments. The invention also contemplates a variety of administration routes. For example, the active substances may be administered by the following routes: intravenous, subcutaneous, intraperitoneal, intramuscular, oral, anal (i.e., via suppository formulations), or pulmonary (i.e., via inhalers, atomizers, nebulizers, etc.)

In another aspect, the DNA sequence information provided by the present invention makes possible the development, by homologous recombination or "knockout" strategies [see, e.g. Kapecchi, Science, 244:1288-1292 (1989)], of rodents that fail to express a functional 88C or 88-2B chemokine receptor or that express a variant of the receptor. Alternatively, transgenic mice which express a cloned 88-2B or 88C receptor can be prepared by well known laboratory techniques [Manipulating the Mouse Embryo: A Laboratory Manual, Brigid Hohan, Frank Costantini and Elizabeth Lacy, eds. (1986) Cold Spring Harbor Laboratory ISBN 0-87969-175-I]. Such rodents are useful as models for studying the activities of 88C or 88-2B receptors in vivo.

Other aspects and advantages of the present invention will become apparent to one skilled in the art upon consideration of the following examples.

DETAILED DESCRIPTION OF THE INVENTION

The following examples illustrate the invention. Example 1 describes the isolation of genomic DNAs encoding the 88-2B and 88C chemokine receptors. Example 2 presents the isolation and sequencing of cDNAs encoding human 88-2B and 88C and macaque 88C. Example 3 provides a description of Northern analyses revealing the expression patterns of the 88-2B and 88C receptors in a variety of tissues. Example 4 details the recombinant expression of the 88-2B and 88C receptors. Example 5 describes $Ca^{++}$ flux assays, phosphoinositol hydrolysis assays, and binding assays for 88-2B and 88C receptor activity in response to a variety of potential ligands. Experiments describing the role of 88C and 882B as co-receptors for HIV is presented in Examples 6 and 7. The preparation and characterization of monoclonal and polyclonal antibodies immunoreactive with 88C is described in Example 8. Example 9 describes additional assays designed to identify 88-2B or 88C ligands or modulators.

EXAMPLE 1

Partial genomic clones encoding the novel chemokine receptor genes of this invention were isolated by PCR based on conserved sequences found in previously identified genes and based on a clustering of these chemokine receptor genes within the human genome. The genomic DNA was amplified by standard PCR methods using degenerate oligonucleotide primers.

Templates for PCR amplifications were members of a commercially available source of recombinant human genomic DNA cloned into Yeast Artificial Chromosomes (i.e., YACs) (Research Genetics, Inc., Huntsville, Ala., YAC Library Pools, catalog no. 95011 B). A YAC vector can accommodate inserts of 500-1000 kilobase pairs. Initially, pools of YAC clone DNAs were screened by PCR using primers specific for the gene encoding CCCKR1. In particular, CCCKR(2)-5', the sense strand primer (corresponding to the sense strand of CCCKR1), is presented in SEQ ID NO:15. Primer CCCKR (2)-5' consisted of the sequence 5'-CGTAAGCTTA-GAGAAGCCGGGATGGGAA-3', wherein the underlined nucleotides are the translation start codon for CCCKR1. The anti-sense strand primer was CCCKR-3' (corresponding to the anti-sense strand of CCCKR1) and its sequence is presented in SEQ ID NO:16. The sequence of CCCKR-3',5'-GCCTCTAGAGTCAGAGACCAGCAGA-3', contains the reverse complement of the CCCKR1 translation stop codon (underlined). Pools of YAC clone DNAs yielding detectable PCR products (i.e., DNA bands upon gel electrophoresis) identified appropriate sub-pools of YAC clones, based on a proprietary identification scheme (Research Genetics, Inc., Huntsville, Ala.). PCR reactions were initiated with an incubation at 94° C. for four minutes. Sequence amplifications were achieved using 33 cycles of denaturation at 94° C. for one minute, annealing at 55° C. for one minute, and extension at 72° C. for two minutes.

The sub-pools of YAC clone DNAs were then subjected to a second round of PCR reactions using the conditions, and primers, that were used in the first round of PCR. Results from sub-pool screenings identified individual clones capable of supporting PCR reactions with the CCCKR-specific primers. One clone, 881F10, contained 640 kb of human genomic DNA from chromosome 3p21 including the genes for CCCKR1 and CCCKR2, as determined by PCR and hybridization. An overlapping YAC clone, 941A7, contained 700 kb of human genomic DNA and also contained the genes for CCCKR1 and CCCKR2. Consequently, further mapping studies were undertaken using these two YAC clones. Southern analyses revealed that CCCKR1 and CCCKR2 were located within approximately 100 kb of one another.

The close proximity of the CCCKR1 and CCCKR2 genes suggested that novel related genes might be linked to CCCKR1 and CCCKR2. Using DNA from yeast containing YAC clones 881F10 and 941A7 as templates, PCR reactions were performed to amplify any linked receptor genes. Degenerate oligodeoxyribonucleotides were designed as PCR primers. These oligonucleotides corresponded to regions encoding the second intracellular loop and the sixth transmembrane domain of CC chemokine receptors, as deduced from aligned sequence comparisons of CCCKR1, CCCKR2, and V28. V28 was used because it is an orphan receptor that exhibits the characteristics of a chemokine receptor; V28 has also been mapped to human chromosome 3 [Raport et al., *Gene* 163: 295-299 (1995)]. Of further note, the two splice variants of CCCKR2, CCCKR2A and CCCKR2B, are identical in the second intracellular loop and sixth transmembrane domain regions used in the analysis. The 5' primer, designated V28degf2, contains an internal BamHI site (see below); its sequence is presented in SEQ ID NO:5. The sequence of primer V28degf2 corresponds to DNA encoding the second intracellular loop region of the canonical receptor structure. See Probst et al., supra. The 3' primer, designated V28degr2, contains an internal HindIII site (see below); its sequence is presented in SEQ ID NO:6. The sequence of primer V28degr2 corresponds to DNA encoding the sixth transmembrane domain of the canonical receptor structure.

Amplified PCR DNA was subsequently digested with BamHI and HindIII to generate fragments of approximately 390 bp, consistent with the fragment size predicted from inspection of the canonical sequence. Following endonuclease digestion, these PCR fragments were cloned into pBluescript (Stratagene Inc., LaJolla, Calif.). A total of 54 cloned fragments were subjected to automated nucleotide sequence analyses. In addition to sequences from CCCKR1 and CCCKR2, sequences from the two novel chemokine receptor genes of the invention were identified. These two novel chemokine receptor genes were designated 88-2B and 88C.

Restriction endonuclease mapping and hybridization were utilized to map the relative positions of genes encoding the receptors 88C, 88-2B, CCCKR1, and CCCKR2. These four genes are closely linked, as the gene for 88C is approximately 18 KBP from the CCCKR2 gene on human chromosome 3p21.

EXAMPLE 2

Full-length 88-2B and 88C cDNAs were isolated from a macrophage cDNA library by the following procedure. Initially, a cDNA library, described in Tjoelker et al., *Nature* 374:549-553 (1995), was constructed in pRc/CMV (Invitrogen Corp., San Diego, Calif.) from human macrophage mRNA. The cDNA library was screened for the presence of 88-2B and 88C cDNA clones by PCR using unique primer pairs corresponding to 88-2B or 88C. The PCR protocol involved an initial denaturation at 94° C. for four minutes. Polynucleotides were then amplified using 33 cycles of PCR under the following conditions: Denaturation at 94° C. for one minute, annealing at 55° C. for one minute, and extension at 72° C. for two minutes. The first primer specific for 88-2B was primer 88-2B-f1, presented in SEQ ID NO:11. It corresponds to the sense strand of SEQ ID NO:3 at nucleotides 844-863. The second PCR primer specific for the gene encoding 88-2B was primer 88-2B-r1, presented in SEQ ID NO:12; the 88-2B-r1 sequence corresponds to the anti-sense strand of SEQ ID NO:3 at nucleotides 1023-1042. Similarly, the sequence of the first primer specific for the gene encoding 88C, primer 88C-f1, is presented in SEQ ID NO:13 and corresponds to the sense strand of SEQ ID NO:1 at nucleotides 453-471. The second primer specific for the gene encoding 88C is primer 88C-r3, presented in SEQ ID NO:14; the sequence of 88C-r3 corresponds to the anti-sense strand of SEQ ID NO:1 at nucleotides 744-763.

The screening identified clone 777, a cDNA clone of 88-2B. Clone 777 contained a DNA insert of 1915 bp including the full length coding sequence of 88-2B as determined by the following criteria: the clone contained a long open reading frame beginning with an ATG codon, exhibited a Kozak sequence, and had an in-frame stop codon upstream. The DNA and deduced amino acid sequences of the insert of clone 777 are presented in SEQ ID NO:3 and SEQ ID NO:4, respectively. The 88-2B transcript was relatively rare in the macrophage cDNA library. During the library screen, only three 88-2B clones were identified from an estimated total of three million clones.

Screening for cDNA clones encoding the 88C chemokine receptor identified clones 101 and 134 which appeared to contain the entire 88C coding region, including a putative initiation codon. However, these clones lacked the additional 5' sequence needed to confirm the identity of the initiation codon. The 88C transcript was relatively abundant in the macrophage cDNA Library. During the library screen, it was estimated that 88C was present at one per 3000 transcripts (in a total of approximately three million clones in the library).

RACE PCR (Rapid Amplification of cDNA Ends) was performed to extend existing 88C clone sequences, thereby facilitating the accurate characterization of the 5' end of the 88C cDNA. Human spleen 5'-RACE-ready cDNA was purchased from Clontech Laboratories, Inc., Palo Alto, Calif., and used according to the manufacturer's recommendations. The cDNA had been made "5'-RACE-ready" by ligating an anchor sequence to the 5' ends of the cDNA fragments. The anchor sequence is complementary to an anchor primer supplied by Clontech Laboratories, Inc., Palo Alto, Calif. The anchor sequence-anchor primer duplex polynucleotide contains an EcoRI site. Human spleen cDNA was chosen as template DNA because Northern blots had revealed that 88C was expressed in this tissue. The PCR reactions were initiated by denaturing samples at 94° C. for four minutes. Subsequently, sequences were amplified using 35 cycles involving denaturation at 94° C. for one minute, annealing at 60° C. for 45 seconds, and extension at 72° C. for two minutes. The first round of PCR was performed on reaction mixtures containing 2 µl of the 5'-RACE-ready spleen cDNA, 1 µl of the anchor primer, and 1 µl of primer 88c-r4 (100 ng/µl) in a total reaction volume of 50 µl. The 88C-specific primer, primer 88c-r4 (5'-GATAAGCCTCACAGCCCTGTG-3'), is presented in SEQ ID NO:7. The sequence of primer 88c-r4 corresponds to the anti-sense strand of SEQ ID NO:1 at nucleotides 745-765.

A second round of PCR was performed on reaction mixtures including 1 μl of the first PCR reaction with 1 μl of anchor primer and 1 μl of primer 88C-rlb (100 ng/μl) containing the following sequence (5'-GCTAAGCTTGATGACTATCTT-TAATGTC-3') and presented in SEQ ID NO:8. The sequence of primer 88C-rlb contains an internal HindIII cloning site (underlined). The sequence 3' of the HindIII site corresponds to the anti-sense strand of SEQ ID NO:1 at nucleotides 636-654. The resulting PCR product was digested with EcoRI and HindIII and fractionated on a 1% agarose gel. The approximately 700 bp fragment was isolated and cloned into pBluescript. Clones with the largest inserts were sequenced. Alternatively, the intact PCR product was ligated into vector pCR using a commercial TA cloning kit (Invitrogen Corp., San Diego, Calif.) for subsequent nucleotide sequence determinations.

The 88-2B and 88C cDNAs were sequenced using the PRISM™ Ready Reaction DyeDeoxy™ Terminator Cycle Sequencing Kit (Perkin Elmer Corp., Foster City, Calif.) and an Applied Biosystems 373A DNA Sequencer. The insert of clone 777 provided the double-stranded template for sequencing reactions used to determine the 88-2B cDNA sequence. The sequence of the entire insert of clone 777 was determined and is presented as the 88-2B cDNA sequence and deduced amino acid sequence in SEQ ID NO:3. The sequence is 1915 bp in length, including 361 bp of 5' untranslated DNA (corresponding to SEQ ID NO:3 at nucleotides 1-361), a coding region of 1065 bp (corresponding to SEQ ID NO:3 at nucleotides 362-1426), and 489 bp of 3' untranslated DNA (corresponding to SEQ ID NO:3 at nucleotides 1427-1915). The 88-2B genomic DNA, described in Example 1 above, corresponds to SEQ ID NO:3 at nucleotides 746-1128. The 88C cDNA sequence, and deduced amino acid sequence, is presented in SEQ ID NO:1. The 88C cDNA sequence is a composite of sequences obtained from RACE-PCR cDNA, clone 134, and clone 101. The RACE-PCR cDNA was used as a sequencing template to determine nucleotides 1-654 in SEQ ID NO:1, including the unique identification of 9 bp of 5' untranslated cDNA sequence in SEQ ID NO:1 at nucleotides 1-9. The sequence obtained from the RACE PCR cDNA confirmed the position of the first methionine codon at nucleotides 55-57 in SEQ ID NO:1, and supported the conclusion that clone 134 and clone 101 contained full-length copies of the 88C coding region. Clone 134 contained 45 bp of 5' untranslated cDNA (corresponding to SEQ ID NO:1 at nucleotides 10-54), the 1056 bp 88C coding region (corresponding to SEQ ID NO:1 at nucleotides 55-1110), and 492 bp of 3' untranslated cDNA (corresponding to SEQ ID NO:1 at nucleotides 1111-1602). Clone 101 contained 25 bp of 5' untranslated cDNA (corresponding to SEQ ID NO:1 at nucleotides 30-54), the 1056 bp 88C coding region (corresponding to SEQ ID NO:1 at nucleotides 55-1110), and 2273 bp of 3' untranslated cDNA (corresponding to SEQ ID NO:1 at nucleotides 1111-3383). The 88C genomic DNA described in Example 1 above, corresponds to SEQ ID NO:1 at nucleotides 424-809.

The deduced amino acid sequences of 88-2B and 88C revealed hydrophobicity profiles characteristic of GPCRs, including seven hydrophobic domains corresponding to GPCR transmembrane domains. Sequence comparisons with other GPCRs also revealed a degree of identity. Significantly, the deduced amino acid sequences of both 88-2B and 88C had highest identity with the sequences of the chemokine receptors. Table 1 presents the results of these amino acid sequence comparisons.

TABLE 1

| Chemokine Receptors | 88-2B | 88C |
|---|---|---|
| IL-8RA | 30% | 30% |
| IL-8RB | 31% | 30% |
| CCCKR1 | 62% | 54% |
| CCCKR2A | 46% | 66% |
| CCCKR2B | 50% | 72% |
| 88-2B | 100% | 50% |
| 88-C | 50% | 100% |

Table 1 shows that 88-2B is most similar to CCCKR1 (62% identical at the amino acid level) and 88C is most similar to CCCKR2 (72% identical at the amino acid level).

The deduced amino acid sequences of 88-2B and 88C also reveal the intracellular and extracellular domains characteristic of GPCRs. The 88-2B extracellular domains correspond to the amino acid sequence provided in SEQ ID NO:3, and SEQ ID NO:4, at amino acid residues 1-36, 93-107, 171-196, and 263-284. The extracellular domains of 88-2B are encoded by polynucleotide sequences corresponding to SEQ ID NO:3 at nucleotides 362-469, 638-682, 872-949, and 1148-1213. Extracellular domains of 88C include amino acid residues 1-32, 89-112, 166-191, and 259-280 in SEQ ID NO:1 and SEQ ID NO:2. The 88C extracellular domains are encoded by polynucleotide sequences that correspond to SEQ ID NO:1 at nucleotides 55-150, 319-390, 550-627, and 829-894. The intracellular domains of 88-2B include amino acids 60-71, 131-151, 219-240, and 306-355 of SEQ ID NO:3 and SEQ ID NO:4. Those domains are encoded by polynucleotide sequences corresponding to SEQ ID NO:3 at nucleotides 539-574, 752-814, 1016-1081, and 1277-1426, respectively. The 88C intracellular domains include amino acid residues 56-67, 125-145, 213-235, and 301-352 of SEQ ID NO:1 and SEQ ID NO:2. The intracellular domains of 88C are encoded by polynucleotide sequences corresponding to SEQ ID NO:1 at nucleotides 220-255, 427-489, 691-759, and 955-1110.

In addition, a macaque 88C DNA was amplified by PCR from macaque genomic DNA using primers corresponding to 5' and 3' flanking regions of the human 88C cDNA. The 5' primer corresponded to the region immediately upstream of and including the initiating Met codon. The 3' primer was complementary to the region immediately downstream of the termination codon. The primers included restriction sites for cloning into expression vectors. The sequence of the 5' primer was GACAAGCTTCACAGGGTGGAACAAGATG (with the HindIII site underlined) (SEQ ID NO: 17) and the sequence of the 3' primer was GTCTCTAGACCACT-TGAGTCCGTGTCA (with the XbaI site underlined) (SEQ ID NO: 18). The conditions of the PCR amplification were 94° C. for eight minutes, then 40 cycles of 94° C. for one minute, 55° C. for 45 seconds, and 72° C. one minute. The amplified products were cloned into the HindIII and XbaI sites of pcDNA3 and a clone was obtained and sequenced. The full length macaque cDNA and deduced amino acid sequences are presented in SEQ ID NOs: 19 and 20, respectively. The nucleotide sequence of macaque 88C is 98% identical to the human 88C sequence. The deduced amino acid sequences are 97% identical.

EXAMPLE 3

The mRNA expression patterns of 88-2B and 88C were determined by Northern blot analyses.

Northern blots containing immobilized poly A+ RNA from a variety of human tissues were purchased from Clontech Laboratories, Inc., Palo Alto, Calif. In particular, the following tissues were examined: heart, brain, placenta, lung, liver, skeletal muscle, kidney, pancreas, spleen, thymus, prostate, testis, ovary, small intestine, colon and peripheral blood leukocytes.

A probe specific for 88-2B nucleotide sequences was generated from cDNA clone 478. The cDNA insert in clone 478 contains sequence corresponding to SEQ ID NO: 3 at nucleotides 641-1915. To generate a probe, clone 478 was digested and the insert DNA fragment was isolated following gel electrophoresis. The isolated insert fragment was then radiolabeled with $^{32}$P-labeled nucleotides, using techniques known in the art.

A probe specific for 88C nucleotide sequences was generated by isolating and radiolabeling the insert DNA fragment found in clone 493. The insert fragment from clone 493 contains sequence corresponding to SEQ ID NO: 1 at nucleotides 421-1359. Again, conventional techniques involving $^{32}$P-labeled nucleotides were used to generate the probe.

Northern blots probed with 88-2B revealed an approximately 1.8 kb mRNA in peripheral blood leukocytes. The 88C Northerns showed an approximately 4 kb mRNA in several human tissues, including a strong signal when probing spleen or thymus tissue and less intense signals when analyzing mRNA from peripheral blood leukocytes and small intestine. A relatively weak signal for 88C was detected in lung tissue and in ovarian tissue.

The expression of 88C in human T-cells and in hematopoietic cell lines was also determined by Northern blot analysis. Levels of 88C in CD4$^+$ and CD8$^+$ T-cells were very high. The transcript was present at relatively high levels in myeloid cell lines THP1 and HL-60 and also found in the B cell line Jijoye. In addition, the cDNA was a relatively abundant transcript in a human macrophage cDNA library based on PCR amplification of library subfractions.

EXAMPLE 4

The 88-2B and 88C cDNAs were expressed by recombinant methods in mammalian cells.

For transient transfection experiments, 88C was subcloned into the mammalian cell expression vector pBJ1 [Ishi et al., *J. Biol. Chem* 270:16435-16440 (1995)]. The construct included sequences encoding a prolactin signal sequence for efficient cell surface expression and a FLAG epitope at the amino terminus of 88C to facilitate detection of the expressed protein. The FLAG epitope consists of the sequence "DYKD-DDD." COS-7 cells were transiently transfected with the 88C expression plasmid using Lipofectamine (Life Technology, Inc., Grand Island, N.Y.) following the manufacturer's instructions. Briefly, cells were seeded in 24-well plates at a density of 4×10$^4$ cells per well and grown overnight. The cells were then washed with PBS, and 0.3 mg of DNA mixed with 1.5 µl of lipofectamine in 0.25 ml of Opti-MEM was added to each well. After 5 hours at 37° C., the medium was replaced with medium containing 10% FCS. quantitative ELISA confirmed that 88C was expressed at the cell surface in transiently transfected COS-7 cells using the M1 antibody specific for the FLAG epitope (Eastman Co., New Haven, Conn.).

The FLAG-tagged 88C receptor was also stably transfected into HEK-293 cells, a human embryonic kidney cell line, using transfection reagent DOTAP (N-[1-[(2,3-Dioleoyloxy)propyl]-N,N,N-trimethyl-ammoniummethylsulfate, Boehringer-Mannheim, Inc., Indianapolis, Ind.) according to the manufacturer's recommendations. Stable lines were selected in the presence of the drug G418. The transfected HEK-293 cells were evaluated for expression of 88C at the cell surface by ELISA, using the M1 antibody to the FLAG epitope. ELISA showed that 88C tagged with the FLAG epitope was expressed at the cell surface of stably transformed HEK-293 Cells.

The 88-2B and 88C cDNAs were used to make stable HEK-293 transfectants. The 88-2B receptor cDNA was cloned behind the cytomegalovirus promoter in pRc/CMV (Invitrogen Corp., San Diego, Calif.) using a PCR-based strategy. The template for the PCR reaction was the cDNA insert in clone 777. The PCR primers were 88-2B-3 (containing an internal XbaI site) and 88-2B-5 (containing an internal HindIII site). The nucleotide sequence of primer 88-2B-3 is presented in SEQ ID NO:9; the nucleotide sequence of primer 88-2B-5 is presented in SEQ ID NO:10. An 1104 bp region of cDNA was amplified. Following amplification, the DNA was digested with XbaI and HindIII and cloned into similarly digested pRc/CMV. The resulting plasmid was named 777XP2, which contains 18 bp of 5' untranslated sequence, the entire coding region of 88-2B, and 3 bp of 3' untranslated sequence. For the 88C sequence, the full-length cDNA insert in clone 134 was not further modified before transfecting HEK-293 cells.

To create stably transformed cell lines, the pRc/CMV recombinant clones were transfected using transfection reagent DOTAP (N-[1-[(2,3-Dioleoyloxy)propyl]-N,N,N-trimethyl-ammoniummethylsulfate, Boehringer-Mannheim, Inc., Indianapolis, Ind.) according to the manufacturer's recommendations, into HEK-293 cells, a human embryonic kidney cell line. Stable lines were selected in the presence of the drug G418. Standard screening procedures (i.e., Northern blot analyses) were performed to identify stable cell lines expressing the highest levels of 88-2B and 88C mRNA.

EXAMPLE 5

A. Ca$^{++}$ Flux Assays

To analyze polypeptide expression, a functional assay for chemokine receptor activity was employed. A common feature of signaling through the known chemokine receptors is that signal transduction is associated with the release of intracellular calcium cations. Therefore, intracellular Ca$^{++}$ concentration in the transfected HEK-293 cells was assayed to determine whether the 88-2B or 88C receptors responded to any of the known chemokines.

HEK-293 cells, stably transfected with 88-2B, 88C (without the FLAG epitope sequence), or a control coding region (encoding IL8R or CCCKR2, see below) as described above, were grown in T75 flasks to approximately 90% confluence in MEM+10% serum. Cells were then washed, harvested with versene (0.6 mM EDTA, 10 mM Na$_2$HPO$_4$, 0.14 M NaCl, 3 mM KCl, and 1 mM glucose), and incubated in MEM+10% serum+1 µM Fura-2 AM (Molecular Probes, Inc., Eugene, Oreg.) for 30 minutes at room temperature. Fura-2 AM is a Ca$^{++}$-sensitive dye. The cells were resuspended in Dulbecco's phosphate-buffered saline containing 0.9 mM CaCl$_2$ and 0.5 mM MgCl$_2$ (D-PBS) to a concentration of approximately 10$^7$ cells/ml and changes in fluorescence were monitored using a fluorescence spectrophotometer (Hitachi Model F-4010). Approximately 10$^6$ cells were suspended in 1.8 ml D-PBS in a cuvette maintained at 37° C. Excitation wavelengths alternated between 340 and 380 nm at 4 second intervals; the emission wavelength was 510 nm. Test compositions were added to the cuvette via an injection port; maximal Ca$^{++}$ flux was measured upon the addition of ionomycin.

Positive responses were observed in cells expressing IL-8RA when stimulated with IL-8 and also when CCCKR2 was stimulated with MCP-1 or MCP-3. However, HEK-293 cells expressing either 88-2B or 88C failed to show a flux in intracellular $Ca^{++}$ concentration when exposed to any of the following chemokines: MCP-1, MCP-2, MCP-3, MIP-1α, MIP-1β, IL8, NAP-2, gro/MGSA, IP-10, ENA-78, or PF-4. (Peprotech, Inc., Rocky Hill, N.J.).

Using a more sensitive assay, a $Ca^{++}$ flux response to RANTES was observed microscopically in Fura-2 AM-loaded cells expressing 88-2B. The assay involved cells and reagents-prepared as described above. RANTES (Regulated on Activation, Normal T Expressed and Secreted) is a CC chemokine that has been identified as a chemoattractant and activator of eosinophils. See Neote et al., supra. This chemokine also mediates the release of histamine by basophils and has been shown to function as a chemoattractant for memory T cells in vitro. Modulation of 88-2B receptor activities is therefore contemplated to be useful in modulating leukocyte activation.

FLAG tagged 88C receptor was expressed in HEK-293 cells and tested for chemokine interactions in the $CA^{++}$ flux assay. Cell surface expression of 88C was confirmed by ELISA and by FACScan analysis using the M1 antibody. The chemokines RANTES, MIP-1α, and MIP-1β all induced a $Ca^{++}$ flux in 88C-transfected cells when added at a concentration of 100 nM.

$Ca^{++}$ flux assays can also be designed to identify modulators of chemokine receptor binding. The preceding fluorimetric or microscopic assays are carried out in the presence of test compounds. If $Ca^{++}$ flux is increased in the presence of a test compound, that compound is an activator of chemokine receptor binding. In contrast, a diminished $Ca^{++}$ flux identifies the test compound as an inhibitor of chemokine receptor binding.

B. Phosphoinositol Hydrolysis

Another assay for ligands or modulators involves monitoring phospholipase C activity, as described in Hung et al., *J. Biol. Chem.* 116:827-832 (1992). Initially, host cells expressing a chemokine receptor are loaded with $^3H$-inositol for 24 hours. Test compounds (i.e., potential ligands) are then added to the cells and incubated at 37° C. for 15 minutes. The cells are then exposed to 20 mM formic acid to solubilize and extract hydrolyzed metabolites of phosphoinositol metabolism (i.e., the products of phospholipase C-mediated hydrolysis). The extract is subjected to anion exchange chromatography using an AG1X8 anion exchange column (formate form). Inositol phosphates are eluted with 2 M ammonium formate/0.1 M formic acid and the $^3H$ associated with the compounds is determined using liquid scintillation spectrophotometry. The phospholipase C assay can also be exploited to identify modulators of chemokine receptor activity. The aforementioned assay is performed as described, but with the addition of a potential modulator. Elevated levels of detectable label would indicate the modulator is an activator; depressed levels of the label would indicate the modulator is an inhibitor of chemokine receptor activity.

The phospholipase C assay was performed to identify chemokine ligands of the FLAG-tagged 88C receptor. Approximately 24 hours after transfection, COS-7 cells expressing 88C were labeled for 20-24 hours with myo-[2-$^3H$]inositol (1 μCi/ml) in inositol-free medium containing 10% dialyzed FCS. Labeled cells were washed with inositol-free DMEM containing 10 mM LiCl and incubated at 37° C. for 1 hour with inositol-free DMEM containing 10 mM LiCl and one of the following chemokines: RANTES, MIP-1β, MIP-1α, MCP-1, IL-8, or the murine MCP-1 homolog JE. Inositol phosphate (IP) formation was assayed as described in the previous paragraph. After incubation with chemokines, the medium was aspirated and cells were lysed by addition of 0.75 ml of ice-cold 20 mM formic acid (30 min). Supernatant fractions were loaded onto AG1-X8 Dowex columns (Biorad, Hercules, Calif.), followed by immediate addition of 3 ml of 50 mM $NH_4OH$. The columns were then washed with 4 ml of 40 mM ammonium formate, followed by elution with 2 M ammonium formate. Total inositol phosphates were quantitated by counting beta-emissions.

Because it has been shown that some chemokine receptors, such as IL8RA AND IL8RB, require contransfection with an exogenous G protein before signaling can be detected in COS-7 cells, the 88C receptor was co-expressed with the chimeric G protein Gqi5 (Conklin, et al., *Nature* 363:274-276, (1993). Gqi5 ia a G protein which has the carboxyl terminal five amino acids of Gi (which bind to the receptor) spliced onto Gαq. Co-transfection with Gqi5 significantly potentiates signaling by CCCKR1 and CCKR2B. Co-transfection with Gqi5 revealed that 88C signaled well in response to RANTES, MIP-1β, and MIP-1α, but not in response to MCP-1, IL-8 or the murine MCP-1 homologue JE. Dose-response curves revealed $EC_{50}$ values of 1 nM for RANTES, 6 nM for MIP-1β, and 22 nM for MIP-1α.

88C is the first cloned human receptor with a signaling response to MIP-1β. Compared with other CC chemokines, MIP-1β clearly has a unique cellular activation pattern. It appears to activate T cells but not monocytes (Baggiolini et al., supra) which is consistent with receptor stimulation studies. For example, while MIP-1β binds to CCCKR1, it does not induce calcium flux (Neote et al., supra). In contrast, MIP-1αand RANTES bind to and causes signaling in CCCKR1 and CCCKR5 (RANTES also causes activation of CCCKR3). MIP-1β thus appears to be much more selective than other chemokines of the CC chemokine family. Such selectivity is of therapeutic significance because a specific beneficial activity can be stimulated (such as suppression of HIV infection) without stimulating multiple leukocyte populations which results in general pro-inflammatory activities.

C. Binding Assays

Another assay for receptor interaction with chemokines was a modification of the binding assay described by Ernst et al., *J. Immunol.* 152:3541-3549 (1994). MIP-1β as labeled using the Bolton and Hunter reagent (di-iodide, NEN, Wilmington, Del.), according to the manufacturer's instructions. Unconjugated iodide was separated from labeled protein by elution using a PD-10 column (Pharmacia) equilibrated with PBS and BSA (1% w/v). The specific activity was typically 2200 Ci/mmole. Equilibrium binding was performed by adding $^{125}I$-labeled ligand with or without a 100-fold excess of unlabeled ligand, to $5 \times 10^5$ HEK-293 cells transfected with 88C tagged with the FLAG epitope in polypropylene tubes in a total volume of 300 μl (50 mM HEPES pH 7.4, 1 mM $CaCl_2$, $MgCl_2$, 0.5% BSA) and incubating for 90 minutes at 27° C. with shaking at 150 rpm. The cells were collected, using a Skatron cell harvester (Skatron Instruments Inc., Sterling, Va.), on glass fiber filters presoaked in 0.3% polyethylene-imine and 0.2% BSA. After washing, the filters were removed and bound ligand was quantitated by counting gamma emissions. Ligand binding by competition with unlabeled ligand was determined by incubation of $5 \times 10^5$ transfected cells (as above) with 1.5 nM of radiolabeled ligand and the indicated concentrations of unlabeled ligand. The samples were collected, washed and counted as above. The data was analyzed using the curve-fitting program Prism (GraphPad Inc., San Diego, Calif.) and the iterative non-linear regression program, LIGAND (PM220).

In equilibrium binding assays, 88C receptor bound radiolabeled MIP-1β in a specific and saturable manner. Analysis of this binding data by the method of Scatchard revealed a dissociation constant (Kd) of 1.6 nM. Competition binding assays using labeled MIP-1β revealed high-affinity binding of MIP-1β ($IC_{50}$=7.4 nM), RANTES ($IC_{50}$=6.9 nM), and MIP-1α ($IC_{50}$=7.4 nM), consistent with the signaling data obtained in transiently transfected COS-7 cells as discussed in section B above.

EXAMPLE 6

The chemokines MIP-1α, MIP-1β and RANTES have been shown to inhibit replication of HIV-1 and HIV-2 in human peripheral blood mononuclear cells and PM 1 cells (Cocchi et al., supra). In view of this finding and in view of the results described in Example 5, the present invention contemplates that activation of or ligand binding to the 88C receptor may provide a protective role in HIV infection.

Recently, it has been reported that the orphan G protein-coupled receptor, fusin, can act as a co-receptor for HIV entry. Fusin/CXCR4 in combination with CD4, the primary HIV receptor, apparently facilitates HIV infection of cultured T cells ([Feng et al., Science 272:872-877 (1996)]. Based upon the homology of fusin to chemokine receptors and the chemokine binding profile of 88C, and because 88C is constitutively expressed in T cells and abundantly expressed in macrophages, 88C is likely to be involved in viral and HIV infection.

The function of 88C and 88-2B as co-receptors for HIV was determined by transfecting cells which express CD4 with 88C or 88-2B and challenging the co-transfected cells with HIV. Only cells expressing both CD4 and a functional co-receptor for HIV become infected. HIV infection can be determined by several methods. ELISAs which test for expression of HIV antigens are commercially available, for example Coulter HIV-1 $p24$ antigen assay (U.S. Pat. No. 4,886,742), Coulter Corp., 11800 SW 147th Ave., Miami, Fla. 33196. Alternatively, the test cells can be engineered to express a reporter gene such as LACZ attached to the HIV LTR promoter [Kimpton et al.,. J. Virol. 66:2232-2239 (1992)]. In this method, cells that are infected with HIV are detected by a colorimetric assay.

88C was transiently transfected into a cat cell line, CCC [Clapham, et al., 181:703-715 (1991)], which had been stably tranformed to express human CD4 (CCC-CD4). These cells are normally resistant to infection by any strain of HIV-1 because they do not endogenously express 88C. In these experiments, CCC/CD4 cells were transiently transfected with 88C cloned into the expression vector pcDNA3.1 (Invitrogen Corp., San Diego, Calif.) using lipofectamine (Gibco BRL, Gaithersburg, Md.). Two days after transfection, cells were challenged with HIV. After 4 days of incubation, cells were fixed and stained for p24 antigen as a measure of HIV infection. 88C expression by these cells rendered them susceptible to infection by several strains of HIV-1. These strains included four primary non-syncytium-inducing HIV-1 isolates (M23, E80, SL-2 and SF-162) which were shown to use only 88C as a co-receptor but not fusin. Several primary syncytium-inducing strains of HIV-1 (2006, M13, 2028 and 2076) used either 88C or fusin as a co-receptor. Also, two established clonal HIV-1 viruses (GUN-1 and 89.6) used either 88C or fusin as a co-receptor.

It has been reported that some strains of HIV-2 can infect certain CD4-negative cell lines, thus implying a direct interaction of HIV-2 with a receptor other than CD4 [Clapham et al., J. Virol. 66:3531-3537 (1992)] For some strains of HIV-2, this infection is facilitated by the presence of soluble CD4 (sCD4). Since 88-2B shares high sequence similarity with other chemokine receptors that act as HIV co-receptors (namely 88C and fusin), 88-2B was considered to be a likely HIV-2 co-receptor. The role of 88-2B as an HIV-2 co-receptor was demonstrated using HIV-2 strain ROD/B. Cat CCC cells which do not endogenously express CD4 were transfected with 88-2B. In these experiments, cells were transfected with pcDNA3.1 containing 88-2B using lipofectamine and infected with HIV-2 48 hours later. Three days after infection, cells were immunostained for the presence of HIV-2 envelope glycoproteins. The presence of sCD4 during HIV-$2_{ROD/B}$ challenge increased the infection of these cells by 10-fold. The entry of HIV-2 into the 88-2B transfected cells could be blocked by the presence of 400-800 ng/ml eotaxin, one of the ligands for 88-2B. The baseline infectivity levels of CCC/88-2B (with no soluble CD4) were equivalent to CCC cells which were not transfected with 88-2B.

The role of 88-2B and 88C as co-receptors for HIV was confirmed by preparing and challenging cell lines stably transformed to express 88C or 88-2B with various strains of HIV and SIV. These results are described in Example 7.

Alternatively, the co-receptor role of 88C and 88-2B can be demonstrated by an experimental method which does not require the use of live virus. In this method, cell lines co-expressing 88C or 88-2B, CD4 and a LACZ reporter gene are mixed with a cell line co-expressing the HIV envelope glycoprotein (ENV) and a transcription factor for the reporter gene construct [Nussbaum et al., J. Virol. 68:5411 (1994)]. Cells expressing a functional co-receptor for HIV will fuse with the ENV expressing cells and thereby allow expression of the reporter gene. In this method, detection of reporter gene product by colorimetric assay indicates that 88C or 88-2B function as a co-receptor for HIV.

The mechanism by which chemokines inhibit viral infection has not yet been elucidated. One possible mechanism involves activation of the receptor by binding of a chemokine. The binding of the chemokine leads to signal transduction events in the cell that renders the cell resistant to viral infection and/or prevents replication of the virus in the cell. Similar to interferon induction, the cell may differentiate such that it is resistant to viral infection, or an antiviral state is established. Alternatively, a second mechanism involves direct interference with viral entry into cells by blocking access of viral envelope glycoproteins to the co-receptor by chemokine binding. In this mechanism, G-protein signaling is not required for chemokine suppression of HIV infection.

To distinguish between two mechanisms by which 88C or 88-2B may function as co-receptors for viral or HIV infection, chemokine binding to the receptor is uncoupled from signal transduction and the effect of the chemokine on suppression of viral infection is determined.

Ligand binding can be uncoupled from signal transduction by the addition of compounds which inhibit G-protein mediated signaling. These compounds include, for example, pertussis toxin and cholera toxin. In addition, downstream effector polypeptides can be inhibited by other compounds such as wortmannin. If G-protein signaling is involved in suppression of viral infection, the addition of such compounds would prevent suppression of viral infection by the chemokine. Alternatively, key residues or receptor domains of 88C or 88-2B receptor required for G-protein coupling can be altered or deleted such that G-protein coupling is altered or destroyed but chemokine binding is not affected.

Under these conditions, if chemokines are unable to suppress viral or HIV infection, then signaling through a G-protein is required for suppression of viral or HIV infection. If however, chemokines are able to suppress viral infection, then G-protein signaling is not required for chemokine suppression of viral infection and the protective effects of chemokines may be due to the chemokine blocking the availability of the receptor for the virus.

Another approach involves the use of antibodies directed against 88C or 88-2B. Antibodies which bind to 88C or 88-2B which can be shown not to elicit G-protein signaling may block access to the chemokine or viral binding site of the receptor. If in the presence of antibodies to 88C or 88-2B, viral infection is suppressed, then the mechanism of the protective effects of chemokines is blocking viral access to its receptor. Feng et al. (1996) reported that antibodies to the amino terminus of the fusin receptor suppressed HIV infection.

EXAMPLE 7

Cell lines were stably transformed with 88C or 88-2B to further delineate the role of 88C and 88-2B in HIV infection. Kimpton and Emerman ["Detection of Replication-Competent and Pseudotyped Human Immunodeficiency Virus with a Sensitive Cell Line on the Basis of Activation of an Integrated Beta-Galactosidase Gene," *J. Virol,* 66 (4):2232-2239 (1992)] previously described an indicator cell line, herein identified as HeLa-MAGI cells. HeLa-MAGI cells are HeLa cells that have been stably transformed to express CD4 as well as integrated HIV-1 LTR which drives expression of a nuclear localized β-galactosidase gene. Integration of an HIV provirus in the cells leads to production of the viral transactivator, Tat, which then turns on expression of the β-galactosidase gene. The number of cells that stain positive with X-gal for β-galactosidase activity in situ is directly proportional to the number of infected cells.

These HeLa-MAGI cells can detect lab-adapted isolates of HIV-1 but only a minority of primary isolates [Kimpton and Emerman, supra], and cannot detect most SIV isolates [Chackerian et al., "Characterization of a CD4-Expressing Macaque Cell Line that can Detect Virus After A Single Replication Cycle and can be infected by Diverse Simian Immunodeficiency Virus Isolates," *Virology,* 213 (2):6499-6505 (1995)].

In addition, Harrington and Geballe ["Co-Factor Requirement for Human Immunodeficiency Virus Type 1 Entry into a CD4-Expressing Human Cell Line, *J. Virol.,* 67:5939-5947 (1993)] described a cell line based on U373 cells that had been engineered to express CD4 and the same LTR-β-galactosidase construct. It was previously shown that this cell line, herein identified as U373-MAGI, could not be infected with any HIV (M or T-tropic) strain of HIV, but could be rendered susceptible to infection by fusion with HeLa cells (Harrington and Geballe, supra).

In order to construct indicator cell lines that could detect either macrophage or T cell tropic viruses, epitope-tagged 88C or 88-2B encoding DNA was transfected into HeLa-MAGI or U373-MAGI cells by infection with a retroviral vector to generate HeLa-MAGI-88C or U373-MAGI-88C cell lines, respectively. Expression of the co-receptors on the cell surface was demonstrated by immunostaining live cells using the anti-FLAG M1 antibody and by RT-PCR.

The 88C and 88-2B genes utilized to construct HeLa-MAGI-88C and U373-MAGI-88C included sequences encoding the prolactin signal peptide followed by a FLAG epitope as described in Example 4. This gene was inserted into the retroviral vector pBabe-Puro [Morgenstern and Land, *Nucleic Acids Research,* 18 (12):3587-3596 (1990)]. High titer retroviral vector stocks pseudotyped with the VSV-G protein were made by transient transfection as described in Bartx et al., *J. Virol.* 70:2324-2331 (1996), and used to infect HeLa-MAGI and U373-MAGI cells. Cells resistant to 0.6 μg/ml puromycin (HeLa) or 1 μg/ml puromycin (U373) were pooled. Each pool contained at least 1000 independent transduction events. An early passage (passage 2) stock of the original HeLa-MAGI cells (Kimpton and Emerman, supra) was used to create HeLa-MAGI-88C cells.

Infections of the indicator cell lines with HIV were performed in 12-well plates with 10-fold serial dilutions of 300 μl of virus in the presence of 30 μg/ml DEAE-Dextran as described (Kimpton and Emerman, supra).

All HIV-1 strains and $SIV_{mac239}$ were all obtained from the NIH AIDS Reference and Reagent Program. Molecular clones of primary $HIV-2_{7312A}$ [Gao et al., "Genetic Diversity of Human Immunodeficiency Virus Type 2: Evidence for Distinct Sequence Subtypes with Differences in Virus Biology," *J. Virol.,* 68 (11):7433-7447 (1992)] and SIVsmPbj1.9 [Dewhurst et al., "Sequence Analysis and Acute Pathogenicity of Molecularly Cloned $SIV_{smm}$-PBj14," *Nature,* 345:636-640 (1990)] were obtained from B. Hahn (UAB). All other $SIV_{mne}$ isolates were obtained from Julie Overbaugh (U. Wash., Seattle). Stocks from cloned proviruses were made by transient transfection of 293 cells. Other viral stocks were made by passage of virus in human peripheral blood mononuclear cells or in CEMx174 cells (for SIV stocks.) Viral stocks were normalized by ELISA or $p24^{gag}$ (Coulter Immunology) or $p27^{gag}$ (Coulter Immunology) for HIV-1 and HIV-2/SIV, respectively, using standards provided by the manufacturer.

U373-MAGI-88C cells and U373-MAGI cells (controls) and were infected with limiting dilutions of a T-tropic strain of HIV-1 ($HIV_{LAI}$), an M-tropic strain ($HIV_{YU-2}$), and an SIV isolate, $SIV_{MAC}239$. Infectivity was measured by counting the number of blue cells per well per volume of virus (Table 2).

TABLE 2

| | titer on cell line (IU/ml)[b] | |
|---|---|---|
| virus strain[a] | U373-MAGI | U373-MAGI-88C |
| $HIV-1_{LAI}$ | <100 | <100 |
| $HIV-1_{YU-2}$ | <100 | $2.2 \times 10^6$ |
| $SIV_{MAC}239$ | $1.2 \times 10^3$ | $4 \times 10^5$ |

[a]Viruses derived by transfection of molecular clones into 293 cells.
[b]Infectious units (IU) per ml is the number of blue cells per well multiplied by the dilution of virus supernatant and normalized to 1 ml final volume.

Two days after infection, cells were fixed and stained for β-galactosidase activity with X-gal. The U373-derived MAGI cells were stained for 120 minutes at 37° C. and the HeLa-derived MAGI cells were stained for 50 minutes at 37° C. Background staining of non-infected cells never exceeded more than approximately three blue cells per well. Only dark blue cells were counted, and syncytium with multiple nuclei were counted as a single infected cell. The infectious titer is the number of blue cells per well multiplied by the dilution of virus and normalized to 1 ml. The titer of $HIV_{YU-2}$ on U373-MAGI-88C cells was $2\times10^6$. In contrast, the titer of $HIV-1_{LAI}$ was less than 100 on U373-MAGI-88C. Thus, the specificity of a particular HIV strain for 88C varied by four orders of magnitude.

Although $SIV_{MAC}239$ infection was increased to $4\times10^5$ in U373-MAGI-88C it also clearly infected U373-MAGI cells (Table 2).

Next, a series of primary uncloned HIV strains and cloned M-tropic strains of HIV-1 were analyzed for their ability to infect indicator cell lines that express 88C.

As described above, HeLa-MAGI and HeLa-MAGI-88C cells were infected with limiting dilutions of various HIV strains. The two cloned M-tropic viruses, $HIV_{JR-CSF}$ and $HIV_{YU-2}$, both infected HeLa-MAGI-88C, but not HeLa-MAGI cells, showing that both strains use 88C as a co-receptor (Table 3, See note c). However, a great disparity in the ability of each of these two viral strains to infect HeLa-MAGI-88C cells was observed, $6.2 \times 10^5$ IU/ml for $HIV_{YU-2}$ and $1.2 \times 10^4$ for $HIV_{JR-CSF}$. The infectivity of virus stock (Table 3) is the number of infectious units per physical particle (represented here by the amount of viral core protein). In addition, it was observed that the infectivity of these two cloned viral strains differed by over 50-fold in viral stocks that were independently prepared.

The variability of infectivity of primary viral isolates was further examined by analyzing a collection of twelve different uncloned virus stocks from three different clades (Table 3). Three clade A primary isolates, three clade E isolates, and three additional clade B isolates from geographically diverse origins were used. With all nine strains, the primary strains of HIV could be detected on HeLa-MAGI-88C cells, but not on HeLa-MAGI cells (Table 3). However, the efficacy of infection varied from five infectious units per ng $p24^{gag}$ to over 100 infectious units per ng $p24^{gag}$ (table 3). These results indicate that absolute infectivity of M-tropic strains varies considerably and is independent of clade. A hypothesis that may explain this discrepancy may involve the affinity of the V3 loop of each viral strain for 88C after CD4 binding [Trkola et al., Nature, 384 (6605):184-187 (1996); Wu et al., Nature, 384 (6605):179-183 (1996)].

TABLE 3

| virus strain[a] | viral sub-type (country of origin)[b] | titer (IU/ml) on HeLa-MAGI-88C[c] | $P24^{gag}$ ng/ml | Infectivity[d] |
|---|---|---|---|---|
| $HIV-1_{YU-2}$ | B (USA) | $6.2 \times 10^5$ | 2200 | 281 |
| $HIV-1_{JR-CSF}$ | B (USA) | 12000 | 2800 | 4.2 |
| $HIV-1_{TH020}$ | E (Thailand) | 4133 | 93 | 44 |
| $HIV-1_{TH021}$ | E (Thailand) | 4967 | 52 | 96 |
| $HIV-1_{TH022}$ | E (Thailand) | 200 | 15 | 13 |
| $HIV-1_{US660}$ | B (USA) | 2367 | 127 | 19 |
| $HIV-1_{UG031}$ | A (Uganda) | 1633 | 71 | 23 |
| $HIV-1_{RW009}$ | A (Rwanda) | 3333 | 158 | 21 |
| $HIV-1_{RW026}$ | A (Rwanda) | 739 | 143 | 5.2 |
| $HIV-1_{US727}$ | B (USA) | 14,067 | 289 | 49 |
| $HIV-1_{US056}$ | B (USA) | 5833 | 284 | 21 |
| $HIV-1_{LAI}$ | B (France) | $2.8 \times 10^5$ | 167 | 1600 |

[a] $HIV-1_{YU-2}$ and $HIV-1_{JR-CSF}$ were derived by transfection of molecular clones. All others were tested as crude supernatants of uncloned viral stocks derived from infection of heterologous peripheral blood mononuclear cells.
[b] Clade designation according to Myers et al., 1995 for the env gene; country of origin refers to the country of residence of the HIV-positive individual from whom blood was obtained for viral isolation (World Health Organization Viral Isolate Program).
[c] Infectious units (IU) per ml is the number of blue cells per well multiplied by the dilution of virus supernatant and normalized to 1 ml final volume. All viruses, except $HIV-1_{LAI}$, had less than 10 IU/ml when tested on HeLa-MAGI cells without 88C. $HIV_{LAI}$, a T-tropic strain, has a titer of $2.8 \times 10^5$ on HeLa-MAGI cells with or without 88C.
[d] Infectivity is the infectious units per ng $P24^{gag}$ (column four divided by column five).

The ability of the HeLa-MAGI-88C cells to detect HIV-2 and other SIV strains was also determined. $HIV-2_{Rod}$ has been reported to use fusin as a receptor even in the absence of CD4 [Endres et al., Cell, 87 (4):745-756 (1996)]. $HIV-2_{Rod}$ is able to infect HeLa-MAGI cells, however its infectivity is enhanced at least 10-fold in HeLa-MagI-88C (Table 4). HeLa cells endogenously express fusin. Thus, the molecular clone of $HIV-2_{Rod}$ is dual tropic, and is able to use 88C as one of its co-receptors in addition to CXCR4. Similarly, a primary strain of $HIV-2_{7312A}$ infected HeLa-MAGI-88C cells and not the HeLa-MAGI cells, indicating that like primary strain of HIV-1, it uses 88C as a receptor.

TABLE 4

| virus strain[a] | reference | titer (IU/ml) on HeLa-MAGI[b] | titer (IU/ml) on HeLa-MAGI-88C | Infectivity on HeLa-MAGI-88C[c] |
|---|---|---|---|---|
| $HIV-2_{ROD9}$ | (Guyader et al., 1987) | 967 | 5900 | 13 |
| $HIV-2_{7312A}$ | (Gao et al., 1994) | <30 | 6500 | 17 |
| $SIV_{MAC}239$ | (Naidu et al., 1988) | <30 | 20900 | 90 |
| $SIV_{MNE}c18$ | (Overbaugh et al., 1991) | <30 | 15700 | 19 |
| $SIV_{MNE}170$ | (Rudensey et al., 1995) | <30 | 10700 | 27 |
| $SIV_{SM}Pbj1.9$ | (Dewhurst et al., 1990) | <30 | 776 | ND[d] |
| $SIV_{AGM}9063$ | (Hirsch et al., 1995) | <30 | 50 | <1 |

[a] HIV-2 stocks, $SIV_{SM}Pbj1.9$, and $SIV_{AGM}9063$ were tested directly after by transfection of molecular clones in 293 cells. All others were derived from transfection of molecular clones and subsequently amplified in CEMx174 cells.
[b] Infectious units (IU) per ml is the number of blue cells per well multiplied by the dilution of virus supernatant and normalized to 1 ml final volume. All viruses in this panel were also negative on HeLa-MAGI-88-2B.
[c] Infectivity is the infectious units (on 88C expressing cells) per ng $P27^{gag}$ determined by ELISA.
[d] ND, not determined.

None of the SIV strains tested infected the HeLa-MAGI cells (Table 4), and none infected HeLa-MAGI cells that expresses 88-2B. This indicates that an alternative co-receptor used by SIV in U373 cells is not expressed in HeLa cells, and is not 88-2B. All SIV strains tested infected the HeLa-MAGI-88C cells to some extent (Table 3) indicating that all of the tested SIV strains use at least 88C as one of their co-receptors.

The classification of M-tropic and T-tropic strains of HIV in the past has often been correlated with another designation "non-syncytium inducing" (NSI), and "syncytium inducing" (SI), respectively. Assays based on the cell lines described herein are sensitive to syncytium formation. The infected cells can form large and small foci of infection containing multiple nuclei (Kimpton and Emerman, supra).

Experiments using multiple different viral strains and U373-MAGI-88C or HeLa-MAGI-88C-indicate that SI/NSI designation is not meaningful because all viral strains formed syncytia if the correct co-receptor was present. These experiments show that syncytium formation is more likely a marker for the presence of an appropriate co-receptor on the infected cell, rather than an indication of tropism. Infection of the HeLa-MAGI-88C cells with SIV strains reported in the literature to be non-syncytium forming strains, in particular, $SIV_{MAC}239$, $SIV_{MNE}c18$, and $SIV_{MNE}170$, was remarkable because the size of the syncytia induced in the monolayer was much larger than those induced by any other the HIV strains.

EXAMPLE 8

15 Mouse monoclonal antibodies which specifically recognize 88C were prepared. The antibodies were produced by immunizing mice with a peptide corresponding to the amino terminal twenty amino acids of 88C. The peptide was conjugated to Keyhole Limpet Cyanin (KLH) according to the manufacturer's directions (Pierce, Imject maleimide activated KLH), emulsified in complete Freund's adjuvant and injected into five mice. Two additional injections of conjugated peptide in incomplete Freund's adjuvant occurred at three week intervals. Ten days after the final injection, serum from each of the five mice was tested for immunoreactivity with the twenty amino acid peptide by ELISA. In addition, the immunoreactivity of the sera were tested against intact 88C receptor expressed on the surface of 293 cells by fluorescence activated cell sorting (FACS). The mouse with the best anti-88C activity was chosen for spleen cell fusion and production of monoclonal antibodies by standard laboratory methods. Five monoclonal cell lines (227K, 227M, 227N, 227P, and 227R) were established which produced antibodies that recognized the peptide by ELISA and the 88C protein on 293 cells by FACS. Each antibody was shown to react only with 88C-expressing 293 cells, but not with 293 cells expressing the closely related MCP receptor (CCCKR-2). Each antibody was also shown to recognize 88C expressed transiently in COS cells.

Rabbit polyclonal antibodies were also generated against 88C. Two rabbits were injected with conjugated amino-terminal peptide as described above. The rabbits were further immunized by four additional injections of the conjugated amino-terminal peptide. Serum from each of the rabbits (2337J and 2470J) was tested by FACS of 293 cells expressing 88C. The sera specifically recognized 88C on the surface of 293 cells.

The five anti-88C monoclonal antibodies were tested for their ability to block infection of cells by SIV, the simian immunodeficiency virus closely related to HIV [Lehner et al., *Nature Medicine*, 2:767 (1996)]. Simian CD4$^+$ T cells, which are normally susceptible to infection by SIV, were incubated with the SIV$_{mac}$32HJ5 clone in the presence of the anti-88C monoclonal antibody supernatants diluted 1:5. SIV infection was measured by determining reverse transcriptase (RT) activity on day nine using the RT detection and quantification method (Quan-T-RT assay kit, Amersham, Arlington Heights, Ill.). Four of the antibodies were able to block SIV infection: antibody 227K blocked by 53%, 227M by 59%, 227N by 47% and 227P by 81%. Antibody 227R did not block SIV infection.

The five monoclonal antibodies raised against human 88C amino-terminal peptide were also tested for reactivity against macaque 88C (SEQ ID NO: 20) (which has two amino acid differences from human 88C within the amino-terminal peptide region). The coding regions of human 88C and macaque 88C were cloned into the expression vector pcDNA3 (Invitrogen). These expression plasmids were used to transfect COS cells using DEAE. The empty vector was used as a negative control. Three days after transfection, cells were harvested and incubated with the five anti-88C monoclonal antibodies and prepared for FACS. The results showed that four of the five antibodies (227K, 227M, 227N, and 227P) recognized macaque 88C while one (227R) did not. All five antibodies recognized the transfected human 88C, and none cross-reacted with cells transfected with vector alone. On Feb. 4, 1997, the Applicants deposited hybridoma cell lines 227P, 227R, and 227M with the American Type Culture Collection (ATCC), which is located at 10801 University Blvd., Manassas, Va. 20110-2209, USA, pursuant to the provisions of the Budapest Treaty. These hybridoma cell lines were accorded ATCC designations HB-12281, HB-12282, and HB-12283, respectively.

EXAMPLE 9

Additional methods may be used to identify ligands and modulators of the chemokine receptors of the invention.

In one embodiment, the invention comprehends a direct assay for ligands. Detectably labeled test compounds are exposed to membrane preparations presenting chemokine receptors in a functional conformation. For example, HEK-293 cells, or tissue culture cells, are transfected with an expression vehicle encoding a chemokine receptor. A membrane preparation is then made from the transfected cells expressing the chemokine receptor. The membrane preparation is exposed to $^{125}$I-labeled test compounds (e.g., chemokines) and incubated under suitable conditions (e.g., 10 minutes at 37° C.). The membranes, with any bound test compounds, are then collected on a filter by vacuum filtration and washed to remove unbound test compounds. The radioactivity associated with the bound test compound is then quantitated by subjecting the filters to liquid scintillation spectrophotometry. The specificity of test compound binding may be confirmed by repeating the assay in the presence of increasing quantities of unlabeled test compound and noting the level of competition for binding to the receptor. These binding assays can also identify modulators of chemokine receptor binding. The previously described binding-assay may be performed with the following modifications. In addition to detectably labeled test compound, a potential modulator is exposed to the membrane preparation. An increased level of membrane-associated label indicates the potential modulator is an activator; a decreased level of membrane-associated label indicates the potential modulator is an inhibitor of chemokine receptor binding.

In another embodiment, the invention comprehends indirect assays for identifying receptor ligands that exploit the coupling of chemokine receptors to G proteins. As reviewed in Linder et al., *Sci. Am.*, 267:56-65 (1992), during signal transduction, an activated receptor interacts with a G protein, in turn activating the G protein. The G protein is activated by exchanging GDP for GTP. Subsequent hydrolysis of the G protein-bound GTP deactivates the G protein. One assay for G protein activity therefore monitors the release of $^{32}P_i$ from [γ-$^{32}$P]-GTP. For example, approximately 5×10$^7$ HEK-293 cells harboring plasmids of the invention are grown in MEM+ 10% FCS. The growth medium is supplemented with 5 mCi/ml [$^{32}$P]-sodium phosphate for 2 hours to uniformly label nucleotide pools. The cells are subsequently washed in a low-phosphate isotonic buffer. One aliquot of washed cells is then exposed to a test compound while a second aliquot of cells is treated similarly, but without exposure to the test compound. Following an incubation period (e.g., 10 minutes), cells are pelleted, lysed and nucleotide compounds fractionated using thin layer chromatography developed with 1 M LiCl. Labeled GTP and GDP are identified by co-developing known standards. The labeled GTP and GDP are then quantitated by autoradiographic techniques that are standard in the art. Relatively high levels of $^{32}$P-labeled GDP identify test compounds as ligands. This type of GTP hydrolysis assay is also useful for the identification of modulators of chemokine receptor binding. The aforementioned assay is performed in the presence of a potential modulator. An intensified signal resulting from a relative increase in GTP hydrolysis, producing $^{32}$P-labeled GDP, indicates a relative increase in receptor activity. The intensified signal therefore identifies the potential modulator as an activator. Conversely, a diminished relative signal for $^{32}$P-labeled GDP, indicative of decreased receptor activity, identifies the potential modulator as an inhibitor of chemokine receptor binding.

The activities of G protein effector molecules (e.g., adenylyl cyclase, phospholipase C, ion channels, and phosphodiesterases) are also amenable to assay. Assays for the activities of these effector molecules have been previously described. For example, adenylyl cyclase, which catalyzes the synthesis of cyclic adenosine monophosphate (cAMP), is activated by G proteins. Therefore, ligand binding to a chemokine receptor that activates a G protein, which in turn activates adenylyl cyclase, can be detected by monitoring cAMP levels in a recombinant host cell of the invention. Implementing appropriate controls understood in the art, an elevated level of intracellular cAMP can be attributed to a ligand-induced increase in receptor activity, thereby identifying a ligand. Again using controls understood in the art, a relative reduction in the concentration of cAMP would indirectly identify an inhibitor of receptor activity. The concentration of cAMP can be measured by a commercial enzyme immunoassay. For example, the BioTrak Kit provides reagents for a competitive immunoassay (Amersham, Inc., Arlington Heights, Ill.). Using this kit according to the manufacturer's recommendations, a reaction is designed that involves competing unlabeled cAMP with cAMP conjugated to horseradish peroxidase. The unlabeled cAMP may be obtained, for example, from activated cells expressing the chemokine receptors of the invention. The two compounds compete for binding to an immobilized anti-cAMP antibody. After the competition reaction, the immobilized horseradish peroxidase-cAMP conjugate is quantitated by enzyme assay using a tetramethylbenzidine/$H_2O_2$ single-pot substrate with detection of colored reaction products occurring at 450 nM. The results provide a basis for calculating the level of unlabeled cAMP, using techniques that are standard in the art. In addition to identifying ligands binding to chemokine receptors, the cAMP assay can also be used to identify modulators of chemokine receptor binding. Using recombinant host cells of the invention, the assay is performed as previously described, with the addition of a potential modulator of chemokine receptor activity. By using controls that are understood in the art, a relative increase or decrease in intracellular cAMP levels reflects the activation or inhibition of adenylyl cyclase activity. The level of adenylyl cyclase activity, in turn, reflects the relative activity of the chemokine receptor of interest. A relatively elevated level of chemokine receptor activity identifies an activator; a relatively reduced level of receptor activity identifies an inhibitor of chemokine receptor activity.

While the present invention has been described in terms of specific embodiments, it is understood that variations and modifications will occur to those skilled in the art. Accordingly, only such limitations as appear in the appended claims should be placed on the invention.

---

We claim:

1. A method of screening for a modulator of 88C receptor activity, comprising the steps of:
   (a) contacting in vitro a composition comprising an 88C receptor with a putative ligand, wherein the 88C receptor comprises the amino acid sequence of SEQ ID NO: 2; and
   (b) detecting binding of the 88C receptor and the putative ligand;
   wherein binding of the 88C receptor with the putative ligand is indicative of the 88C receptor having binding activity for the ligand.

2. The method according to claim 1 further comprising the step of screening a 88C ligand for the ability to affect 88C signal transduction activity, wherein an increase in 88C signal transduction activity indicates the ligand is an activator, or a decrease in 88C signal transduction activity indicates the ligand is an inhibitor.

3. A method for identifying a ligand capable of interacting with the chemokine receptor 88C that comprises (i) SEQ ID NO: 2 or (ii) an extracellular domain having residues 89-112 of SEQ ID NO: 2 and which have biological activity of chemokine receptor 88c, said method comprises the steps of:
   (a) providing a host cell expressing said receptor or a membrane preparation comprising said receptor,
   (b) contacting and incubating said receptor with a ligand, and
   (c) identifying the presence of a ligand that specifically interacts with said receptor.

4. The method according to claim 3, wherein said fragment further comprises the amino acid sequence spanning amino acids 1-32, 56-67, 125-145, 166-191, 213-235, 259-280 or 301-352 of SEQ ID NO: 2.

5. The method according to claim 3, wherein said ligand is labeled.

6. The method according to claim 3, wherein said ligand is an agonist or an antagonist.

7. The method according to claim 3, wherein said interaction is identified by measuring the concentration or level of activity of a component of a signal transduction pathway.

8. The method according to claim 7, wherein said signal transduction pathway is identified by measuring an activity selected from the group consisting of: calcium concentration, IP3 concentration, GTP hydrolysis and phospholipase C activity.

9. The method according to any claim 3, wherein said receptor or said fragment is contacted and incubated with a ligand and a further test compound.

10. The method according to claim 3, wherein said cell or said cell membrane preparation are selected from the group consisting of CHO-KI, HEK293, BHK21 and COS-7.

* * * * *

UNITED STATES PATENT AND TRADEMARK OFFICE
CERTIFICATE OF CORRECTION

PATENT NO. : 7,662,548 B2  Page 1 of 1
APPLICATION NO. : 11/068686
DATED : February 16, 2010
INVENTOR(S) : Gray et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 758 days.

Signed and Sealed this

Thirtieth Day of November, 2010

David J. Kappos
*Director of the United States Patent and Trademark Office*

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
      (A) LENGTH: 3383 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 55..1110

(ix) FEATURE:
      (A) NAME/KEY: misc_feature
      (D) OTHER INFORMATION: /= "88C polynucleotide and amino acid
         sequences"

(xi) SEQUENCE DESCRIPTION: SEQ ID NO: 1:

```
AGAAGAGCTG AGACATCCGT TCCCCTACAA GAAACTCTCC CCGGGTGGAA CAAG ATG        57
                                                              Met
                                                               1

GAT TAT CAA GTG TCA AGT CCA ATC TAT GAC ATC AAT TAT TAT ACA TCG       105
Asp Tyr Gln Val Ser Ser Pro Ile Tyr Asp Ile Asn Tyr Tyr Thr Ser
          5                  10                  15

GAG CCC TGC CAA AAA ATC AAT GTG AAG CAA ATC GCA GCC CGC CTC CTG       153
Glu Pro Cys Gln Lys Ile Asn Val Lys Gln Ile Ala Ala Arg Leu Leu
         20                  25                  30

CCT CCG CTC TAC TCA CTG GTG TTC ATC TTT GGT TTT GTG GGC AAC ATG       201
Pro Pro Leu Tyr Ser Leu Val Phe Ile Phe Gly Phe Val Gly Asn Met
         35                  40                  45
```

```
CTG GTC ATC CTC ATC CTG ATA AAC TGC AAA AGG CTG AAG AGC ATG ACT        249
Leu Val Ile Leu Ile Leu Ile Asn Cys Lys Arg Leu Lys Ser Met Thr
 50              55                  60                  65

GAC ATC TAC CTG CTC AAC CTG GCC ATC TCT GAC CTG TTT TTC CTT CTT        297
Asp Ile Tyr Leu Leu Asn Leu Ala Ile Ser Asp Leu Phe Phe Leu Leu
             70                  75                  80

ACT GTC CCC TTC TGG GCT CAC TAT GCT GCC GCC CAG TGG GAC TTT GGA        345
Thr Val Pro Phe Trp Ala His Tyr Ala Ala Ala Gln Trp Asp Phe Gly
                 85                  90                  95

AAT ACA ATG TGT CAA CTC TTG ACA GGG CTC TAT TTT ATA GGC TTC TTC        393
Asn Thr Met Cys Gln Leu Leu Thr Gly Leu Tyr Phe Ile Gly Phe Phe
            100                 105                 110

TCT GGA ATC TTC TTC ATC ATC CTC CTG ACA ATC GAT AGG TAC CTG GCT        441
Ser Gly Ile Phe Phe Ile Ile Leu Leu Thr Ile Asp Arg Tyr Leu Ala
        115                 120                 125

GTC GTC CAT GCT GTG TTT GCT TTA AAA GCC AGG ACG GTC ACC TTT GGG        489
Val Val His Ala Val Phe Ala Leu Lys Ala Arg Thr Val Thr Phe Gly
130                 135                 140                 145

GTG GTG ACA AGT GTG ATC ACT TGG GTG GTG GCT GTG TTT GCG TCT CTC        537
Val Val Thr Ser Val Ile Thr Trp Val Val Ala Val Phe Ala Ser Leu
                150                 155                 160

CCA GGA ATC ATC TTT ACC AGA TCT CAA AAA GAA GGT CTT CAT TAC ACC        585
Pro Gly Ile Ile Phe Thr Arg Ser Gln Lys Glu Gly Leu His Tyr Thr
            165                 170                 175

TGC AGC TCT CAT TTT CCA TAC AGT CAG TAT CAA TTC TGG AAG AAT TTC        633
Cys Ser Ser His Phe Pro Tyr Ser Gln Tyr Gln Phe Trp Lys Asn Phe
        180                 185                 190

CAG ACA TTA AAG ATA GTC ATC TTG GGG CTG GTC CTG CCG CTG CTT GTC        681
Gln Thr Leu Lys Ile Val Ile Leu Gly Leu Val Leu Pro Leu Leu Val
195                 200                 205

ATG GTC ATC TGC TAC TCG GGA ATC CTA AAA ACT CTG CTT CGG TGT CGA        729
Met Val Ile Cys Tyr Ser Gly Ile Leu Lys Thr Leu Leu Arg Cys Arg
210                 215                 220                 225

AAT GAG AAG AAG AGG CAC AGG GCT GTG AGG CTT ATC TTC ACC ATC ATG        777
Asn Glu Lys Lys Arg His Arg Ala Val Arg Leu Ile Phe Thr Ile Met
                230                 235                 240

ATT GTT TAT TTT CTC TTC TGG GCT CCC TAC AAC ATT GTC CTT CTC CTG        825
Ile Val Tyr Phe Leu Phe Trp Ala Pro Tyr Asn Ile Val Leu Leu Leu
            245                 250                 255

AAC ACC TTC CAG GAA TTC TTT GGC CTG AAT AAT TGC AGT AGC TCT AAC        873
Asn Thr Phe Gln Glu Phe Phe Gly Leu Asn Asn Cys Ser Ser Ser Asn
        260                 265                 270

AGG TTG GAC CAA GCT ATG CAG GTG ACA GAG ACT CTT GGG ATG ACG CAC        921
Arg Leu Asp Gln Ala Met Gln Val Thr Glu Thr Leu Gly Met Thr His
275                 280                 285

TGC TGC ATC AAC CCC ATC ATC TAT GCC TTT GTC GGG GAG AAG TTC AGA        969
Cys Cys Ile Asn Pro Ile Ile Tyr Ala Phe Val Gly Glu Lys Phe Arg
290                 295                 300                 305

AAC TAC CTC TTA GTC TTC TTC CAA AAG CAC ATT GCC AAA CGC TTC TGC       1017
Asn Tyr Leu Leu Val Phe Phe Gln Lys His Ile Ala Lys Arg Phe Cys
                310                 315                 320

AAA TGC TGT TCT ATT TTC CAG CAA GAG GCT CCC GAG CGA GCA AGC TCA       1065
Lys Cys Cys Ser Ile Phe Gln Gln Glu Ala Pro Glu Arg Ala Ser Ser
            325                 330                 335

GTT TAC ACC CGA TCC ACT GGG GAG CAG GAA ATA TCT GTG GGC TTG            1110
Val Tyr Thr Arg Ser Thr Gly Glu Gln Glu Ile Ser Val Gly Leu
        340                 345                 350

TGACACGGAC TCAAGTGGGC TGGTGACCCA GTCAGAGTTG TGCACATGGC TTAGTTTTCA     1170
```

```
TACACAGCCT GGGCTGGGGG TGGGGTGGGA GAGGTCTTTT TTAAAAGGAA GTTACTGTTA    1230

TAGAGGGTCT AAGATTCATC CATTTATTTG GCATCTGTTT AAAGTAGATT AGATCTTTTA    1290

AGCCCATCAA TTATAGAAAG CCAAATCAAA ATATGTTGAT GAAAAATAGC AACCTTTTTA    1350

TCTCCCCTTC ACATGCATCA AGTTATTGAC AAACTCTCCC TTCACTCCGA AAGTTCCTTA    1410

TGTATATTTA AAAGAAAGCC TCAGAGAATT GCTGATTCTT GAGTTTAGTG ATCTGAACAG    1470

AAATACCAAA ATTATTTCAG AAATGTACAA CTTTTTACCT AGTACAAGGC AACATATAGG    1530

TTGTAAATGT GTTTAAAACA GGTCTTTGTC TTGCTATGGG GAGAAAAGAC ATGAATATGA    1590

TTAGTAAAGA AATGACACTT TTCATGTGTG ATTTCCCCTC CAAGGTATGG TTAATAAGTT    1650

TCACTGACTT AGAACCAGGC GAGAGACTTG TGGCCTGGGA GAGCTGGGGA AGCTTCTTAA    1710

ATGAGAAGGA ATTTGAGTTG GATCATCTAT TGCTGGCAAA GACAGAAGCC TCACTGCAAG    1770

CACTGCATGG GCAAGCTTGG CTGTAGAAGG AGACAGAGCT GGTTGGGAAG ACATGGGGAG    1830

GAAGGACAAG GCTAGATCAT GAAGAACCTT GACGGCATTG CTCCGTCTAA GTCATGAGCT    1890

GAGCAGGGAG ATCCTGGTTG GTGTTGCAGA AGGTTTACTC TGTGGCCAAA GGAGGGTCAG    1950

GAAGGATGAG CATTTAGGGC AAGGAGACCA CCAACAGCCC TCAGGTCAGG GTGAGGATGG    2010

CCTCTGCTAA GCTCAAGGCG TGAGGATGGG AAGGAGGGAG GTATTCGTAA GGATGGGAAG    2070

GAGGGAGGTA TTCGTGCAGC ATATGAGGAT GCAGAGTCAG CAGAACTGGG GTGGATTTGG    2130

TTTGGAAGTG AGGGTCAGAG AGGAGTCAGA GAGAATCCCT AGTCTTCAAG CAGATTGGAG    2190

AAACCCTTGA AAAGACATCA AGCACAGAAG GAGGAGGAGG AGGTTTAGGT CAAGAAGAAG    2250

ATGGATTGGT GTAAAAGGAT GGGTCTGGTT TGCAGAGCTT GAACACAGTC TCACCCAGAC    2310

TCCAGGCTGT CTTTCACTGA ATGCTTCTGA CTTCATAGAT TTCCTTCCCA TCCCAGCTGA    2370

AATACTGAGG GGTCTCCAGG AGGAGACTAG ATTTATGAAT ACACGAGGTA TGAGGTCTAG    2430

GAACATACTT CAGCTCACAC ATGAGATCTA GGTGAGGATT GATTACCTAG TAGTCATTTC    2490

ATGGGTTGTT GGGAGGATTC TATGAGGCAA CCACAGGCAG CATTTAGCAC ATACTACACA    2550

TTCAATAAGC ATCAAACTCT TAGTTACTCA TTCAGGGATA GCACTGAGCA AGCATTGAG     2610

CAAAGGGGTC CCATATAGGT GAGGGAAGCC TGAAAAACTA AGATGCTGCC TGCCCAGTGC    2670

ACACAAGTGT AGGTATCATT TTCTGCATTT AACCGTCAAT AGGCAAAGGG GGGAAGGGAC    2730

ATATTCATTT GGAAATAAGC TGCCTTGAGC CTTAAAACCC ACAAAAGTAC AATTTACCAG    2790

CCTCCGTATT TCAGACTGAA TGGGGGTGGG GGGGCGCCT TAGGTACTTA TTCCAGATGC    2850

CTTCTCCAGA CAAACCAGAA GCAACAGAAA AAATCGTCTC TCCCTCCCTT TGAAATGAAT    2910

ATACCCCTTA GTGTTTGGGT ATATTCATTT CAAAGGGAGA GAGAGAGGTT TTTTTCTGTT    2970

CTTTCTCATA TGATTGTGCA CATACTTGAG ACTGTTTTGA ATTGGGGGA TGGCTAAAAC     3030

CATCATAGTA CAGGTAAGGT GAGGGAATAG TAAGTGGTGA GAACTACTCA GGGAATGAAG    3090

GTGTCAGAAT AATAAGAGGT GCTACTGACT TTCTCAGCCT CTGAATATGA ACGGTGAGCA    3150

TTGTGGCTGT CAGCAGGAAG CAACGAAGGG AAATGTCTTT CCTTTTGCTC TTAAGTTGTG    3210

GAGAGTGCAA CAGTAGCATA GGACCCTACC CTCTGGGCCA AGTCAAAGAC ATTCTGACAT    3270

CTTAGTATTT GCATATTCTT ATGTATGTGA AAGTTACAAA TTGCTTGAAA GAAAATATGC    3330

ATCTAATAAA AAACACCTTC TAAAATAAAA AAAAAAAAA AAAAAAAAA AAA             3383
```

(2) INFORMATION FOR SEQ ID NO: 2:

(i) SEQUENCE CHARACTERISTICS:
        (A) LENGTH: 352 amino acids (B) TYPE: amino acid
          (D) TOPOLOGY: linear (ii) MOLECULE TYPE: protein (ix) FEATURE:
         (A) NAME/KEY: misc_feature
         (D) OTHER INFORMATION: /= "88C amino acid sequence"

(xi) SEQUENCE DESCRIPTION: SEQ ID NO: 2:

Met Asp Tyr Gln Val Ser Ser Pro Ile Tyr Asp Ile Asn Tyr Tyr Thr
 1               5                  10                  15

Ser Glu Pro Cys Gln Lys Ile Asn Val Lys Gln Ile Ala Ala Arg Leu
             20                  25                  30

Leu Pro Pro Leu Tyr Ser Leu Val Phe Ile Phe Gly Phe Val Gly Asn
             35                  40                  45

Met Leu Val Ile Leu Ile Leu Ile Asn Cys Lys Arg Leu Lys Ser Met
 50                  55                  60

Thr Asp Ile Tyr Leu Leu Asn Leu Ala Ile Ser Asp Leu Phe Phe Leu
 65                  70                  75                  80

Leu Thr Val Pro Phe Trp Ala His Tyr Ala Ala Ala Gln Trp Asp Phe
             85                  90                  95

Gly Asn Thr Met Cys Gln Leu Leu Thr Gly Leu Tyr Phe Ile Gly Phe
             100                 105                 110

Phe Ser Gly Ile Phe Phe Ile Ile Leu Leu Thr Ile Asp Arg Tyr Leu
             115                 120                 125

Ala Val Val His Ala Val Phe Ala Leu Lys Ala Arg Thr Val Thr Phe
 130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
             165                 170                 175

Thr Cys Ser Ser His Phe Pro Tyr Ser Gln Tyr Gln Phe Trp Lys Asn
             180                 185                 190

Phe Gln Thr Leu Lys Ile Val Ile Leu Gly Leu Val Leu Pro Leu Leu
             195                 200                 205

Val Met Val Ile Cys Tyr Ser Gly Ile Leu Lys Thr Leu Leu Arg Cys
 210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
             245                 250                 255

Leu Asn Thr Phe Gln Glu Phe Phe Gly Leu Asn Asn Cys Ser Ser Ser
             260                 265                 270

Asn Arg Leu Asp Gln Ala Met Gln Val Thr Glu Thr Leu Gly Met Thr
             275                 280                 285

His Cys Cys Ile Asn Pro Ile Ile Tyr Ala Phe Val Gly Glu Lys Phe
             290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
             325                 330                 335

Ser Val Tyr Thr Arg Ser Thr Gly Glu Gln Glu Ile Ser Val Gly Leu
             340                 345                 350

(2) INFORMATION FOR SEQ ID NO: 3:

(i) SEQUENCE CHARACTERISTICS:
    (A) LENGTH: 1915 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 362..1426

(ix) FEATURE:
    (A) NAME/KEY: misc_feature
    (D) OTHER INFORMATION: /= "88-2B polynucleotide and amino acid sequences"

(xi) SEQUENCE DESCRIPTION: SEQ ID NO: 3:

```
ATAATAATGA TTATTATATT GTTATCATTA TCTAGCCTGT TTTTTCCTGT TTTGTATTTC      60

TTCCTTTAAA TGCTTTCAGA AATCTGTATC CCCATTCTTC ACCACCACCC CACAACATTT     120

CTGCTTCTTT TCCCATGCCG GTCATGCTA  ACTTTGAAAG CTTCAGCTCT TTCCTTCCTC     180

AATCCTTTTC CTGGCACCTC TGATATGCCT TTTGAAATTC ATGTTAAAGA ATCCCTAGGC     240

TGCTATCACA TGTGGCATCT TTGTTGAGTA CATGAATAAA TCAACTGGTG TGTTTTACGA     300

AGGATGATTA TGCTTCATTG TGGGATTGTA TTTTTCTTCT TCTATCACAG GGAGAAGTGA     360
```

| A ATG ACA ACC TCA CTA GAT ACA GTT GAG ACC TTT GGT ACC ACA TCC | 406 |
|---|---|
| Met Thr Thr Ser Leu Asp Thr Val Glu Thr Phe Gly Thr Thr Ser | |
| 1           5              10              15 | |

| TAC TAT GAT GAC GTG GGC CTG CTC TGT GAA AAA GCT GAT ACC AGA GCA | 454 |
|---|---|
| Tyr Tyr Asp Asp Val Gly Leu Leu Cys Glu Lys Ala Asp Thr Arg Ala | |
| 20              25              30 | |

| CTG ATG GCC CAG TTT GTG CCC CCG CTG TAC TCC CTG GTG TTC ACT GTG | 502 |
|---|---|
| Leu Met Ala Gln Phe Val Pro Pro Leu Tyr Ser Leu Val Phe Thr Val | |
| 35              40              45 | |

| GGC CTC TTG GGC AAT GTG GTG GTG GTG ATG ATC CTC ATA AAA TAC AGG | 550 |
|---|---|
| Gly Leu Leu Gly Asn Val Val Val Val Met Ile Leu Ile Lys Tyr Arg | |
| 50              55              60 | |

| AGG CTC CGA ATT ATG ACC AAC ATC TAC CTG CTC AAC CTG GCC ATT TCG | 598 |
|---|---|
| Arg Leu Arg Ile Met Thr Asn Ile Tyr Leu Leu Asn Leu Ala Ile Ser | |
| 65              70              75 | |

| GAC CTG CTC TTC CTC GTC ACC CTT CCA TTC TGG ATC CAC TAT GTC AGG | 646 |
|---|---|
| Asp Leu Leu Phe Leu Val Thr Leu Pro Phe Trp Ile His Tyr Val Arg | |
| 80              85              90              95 | |

| GGG CAT AAC TGG GTT TTT GGC CAT GGC ATG TGT AAG CTC CTC TCA GGG | 694 |
|---|---|
| Gly His Asn Trp Val Phe Gly His Gly Met Cys Lys Leu Leu Ser Gly | |
| 100             105             110 | |

| TTT TAT CAC ACA GGC TTG TAC AGC GAG ATC TTT TTC ATA ATC CTG CTG | 742 |
|---|---|
| Phe Tyr His Thr Gly Leu Tyr Ser Glu Ile Phe Phe Ile Ile Leu Leu | |
| 115             120             125 | |

| ACA ATC GAC AGG TAC CTG GCC ATT GTC CAT GCT GTG TTT GCC CTT CGA | 790 |
|---|---|
| Thr Ile Asp Arg Tyr Leu Ala Ile Val His Ala Val Phe Ala Leu Arg | |
| 130             135             140 | |

| GCC CGG ACT GTC ACT TTT GGT GTC ATC ACC AGC ATC GTC ACC TGG GGC | 838 |
|---|---|
| Ala Arg Thr Val Thr Phe Gly Val Ile Thr Ser Ile Val Thr Trp Gly | |
| 145             150             155 | |

| CTG GCA GTG CTA GCA GCT CTT CCT GAA TTT ATC TTC TAT GAG ACT GAA | 886 |
|---|---|
| Leu Ala Val Leu Ala Ala Leu Pro Glu Phe Ile Phe Tyr Glu Thr Glu | |
| 160             165             170             175 | |

| GAG TTG TTT GAA GAG ACT CTT TGC AGT GCT CTT TAC CCA GAG GAT ACA | 934 |
|---|---|
| Glu Leu Phe Glu Glu Thr Leu Cys Ser Ala Leu Tyr Pro Glu Asp Thr | |
| 180             185             190 | |

```
GTA TAT AGC TGG AGG CAT TTC CAC ACT CTG AGA ATG ACC ATC TTC TGT      982
Val Tyr Ser Trp Arg His Phe His Thr Leu Arg Met Thr Ile Phe Cys
            195                 200                 205

CTC GTT CTC CCT CTG CTC GTT ATG GCC ATC TGC TAC ACA GGA ATC ATC     1030
Leu Val Leu Pro Leu Leu Val Met Ala Ile Cys Tyr Thr Gly Ile Ile
            210                 215                 220

AAA ACG CTG CTG AGG TGC CCC AGT AAA AAA AAG TAC AAG GCC ATC CGG     1078
Lys Thr Leu Leu Arg Cys Pro Ser Lys Lys Lys Tyr Lys Ala Ile Arg
225                 230                 235

CTC ATT TTT GTC ATC ATG GCG GTG TTT TTC ATT TTC TGG ACA CCC TAC     1126
Leu Ile Phe Val Ile Met Ala Val Phe Phe Ile Phe Trp Thr Pro Tyr
240                 245                 250                 255

AAT GTG GCT ATC CTT CTC TCT TCC TAT CAA TCC ATC TTA TTT GGA AAT     1174
Asn Val Ala Ile Leu Leu Ser Ser Tyr Gln Ser Ile Leu Phe Gly Asn
            260                 265                 270

GAC TGT GAG CGG AGC AAG CAT CTG GAC CTG GTC ATG CTG GTG ACA GAG     1222
Asp Cys Glu Arg Ser Lys His Leu Asp Leu Val Met Leu Val Thr Glu
            275                 280                 285

GTG ATC GCC TAC TCC CAC TGC TGC ATG AAC CCG GTG ATC TAC GCC TTT     1270
Val Ile Ala Tyr Ser His Cys Cys Met Asn Pro Val Ile Tyr Ala Phe
            290                 295                 300

GTT GGA GAG AGG TTC CGG AAG TAC CTG CGC CAC TTC TTC CAC AGG CAC     1318
Val Gly Glu Arg Phe Arg Lys Tyr Leu Arg His Phe Phe His Arg His
305                 310                 315

TTG CTC ATG CAC CTG GGC AGA TAC ATC CCA TTC CTT CCT AGT GAG AAG     1366
Leu Leu Met His Leu Gly Arg Tyr Ile Pro Phe Leu Pro Ser Glu Lys
320                 325                 330                 335

CTG GAA AGA ACC AGC TCT GTC TCT CCA TCC ACA GCA GAG CCG GAA CTC     1414
Leu Glu Arg Thr Ser Ser Val Ser Pro Ser Thr Ala Glu Pro Glu Leu
            340                 345                 350

TCT ATT GTG TTT TAGGTCAGAT GCAGAAAATT GCCTAAAGAG GAAGGACCAA         1466
Ser Ile Val Phe
            355

GGAGATGAAG CAAACACATT AAGCCTTCCA CACTCACCTC TAAAACAGTC CTTCAAACTT   1526

CCAGTGCAAC ACTGAAGCTC TTGAAGACAC TGAAATATAC ACACAGCAGT AGCAGTAGAT   1586

GCATGTACCC TAAGGTCATT ACCACAGGCC AGGGGCTGGG CAGCGTACTC ATCATCAACC   1646

CTAAAAAGCA GAGCTTTGCT TCTCTCTCTA AAATGAGTTA CCTACATTTT AATGCACCTG   1706

AATGTTAGAT AGTTACTATA TGCCGCTACA AAAGGTAAA ACTTTTTATA TTTTATACAT    1766

TAACTTCAGC CAGCTATTGA TATAAATAAA ACATTTTCAC ACAATACAAT AAGTTAACTA   1826

TTTTATTTTC TAATGTGCCT AGTTCTTTCC CTGCTTAATG AAAAGCTTGT TTTTTCAGTG   1886

TGAATAAATA ATCGTAAGCA ACAAAAAAA                                    1915

(2) INFORMATION FOR SEQ ID NO: 4:

(i) SEQUENCE CHARACTERISTICS:
        (A) LENGTH: 355 amino acids
        (B) TYPE: amino acid
        (D) TOPOLOGY: linear (ii) MOLECULE TYPE: protein (ix) FEATURE:
        (A) NAME/KEY: misc_feature
        (D) OTHER INFORMATION: /= "88-2B amino acid sequence"

(xi) SEQUENCE DESCRIPTION: SEQ ID NO: 4:

Met Thr Thr Ser Leu Asp Thr Val Glu Thr Phe Gly Thr Thr Ser Tyr
 1               5                  10                  15
```

```
Tyr Asp Asp Val Gly Leu Leu Cys Glu Lys Ala Asp Thr Arg Ala Leu
            20                  25                  30

Met Ala Gln Phe Val Pro Pro Leu Tyr Ser Leu Val Phe Thr Val Gly
        35                  40                  45

Leu Leu Gly Asn Val Val Val Met Ile Leu Ile Lys Tyr Arg Arg
    50                  55                  60

Leu Arg Ile Met Thr Asn Ile Tyr Leu Leu Asn Leu Ala Ile Ser Asp
65                  70                  75                  80

Leu Leu Phe Leu Val Thr Leu Pro Phe Trp Ile His Tyr Val Arg Gly
            85                  90                  95

His Asn Trp Val Phe Gly His Gly Met Cys Lys Leu Leu Ser Gly Phe
            100                 105                 110

Tyr His Thr Gly Leu Tyr Ser Glu Ile Phe Phe Ile Ile Leu Leu Thr
            115                 120                 125

Ile Asp Arg Tyr Leu Ala Ile Val His Ala Val Phe Ala Leu Arg Ala
        130                 135                 140

Arg Thr Val Thr Phe Gly Val Ile Thr Ser Ile Val Thr Trp Gly Leu
145                 150                 155                 160

Ala Val Leu Ala Ala Leu Pro Glu Phe Ile Phe Tyr Glu Thr Glu Glu
            165                 170                 175

Leu Phe Glu Glu Thr Leu Cys Ser Ala Leu Tyr Pro Glu Asp Thr Val
            180                 185                 190

Tyr Ser Trp Arg His Phe His Thr Leu Arg Met Thr Ile Phe Cys Leu
            195                 200                 205

Val Leu Pro Leu Leu Val Met Ala Ile Cys Tyr Thr Gly Ile Ile Lys
        210                 215                 220

Thr Leu Leu Arg Cys Pro Ser Lys Lys Lys Tyr Lys Ala Ile Arg Leu
225                 230                 235                 240

Ile Phe Val Ile Met Ala Val Phe Phe Ile Phe Trp Thr Pro Tyr Asn
            245                 250                 255

Val Ala Ile Leu Leu Ser Ser Tyr Gln Ser Ile Leu Phe Gly Asn Asp
            260                 265                 270

Cys Glu Arg Ser Lys His Leu Asp Leu Val Met Leu Val Thr Glu Val
        275                 280                 285

Ile Ala Tyr Ser His Cys Cys Met Asn Pro Val Ile Tyr Ala Phe Val
        290                 295                 300

Gly Glu Arg Phe Arg Lys Tyr Leu Arg His Phe Phe His Arg His Leu
305                 310                 315                 320

Leu Met His Leu Gly Arg Tyr Ile Pro Phe Leu Pro Ser Glu Lys Leu
            325                 330                 335

Glu Arg Thr Ser Ser Val Ser Pro Ser Thr Ala Glu Pro Glu Leu Ser
            340                 345                 350

Ile Val Phe
        355

(2) INFORMATION FOR SEQ ID NO: 5:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (ix) FEATURE:
```

```
         (A) NAME/KEY: misc_feature
         (D) OTHER INFORMATION: /= "V28degf2"

(xi) SEQUENCE DESCRIPTION: SEQ ID NO: 5:

GACGGATCCA TYGAYAGRTA CCTGGCYATY GTCC                        34

(2) INFORMATION FOR SEQ ID NO: 6:

(i) SEQUENCE CHARACTERISTICS:
         (A) LENGTH: 32 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: misc_feature
         (D) OTHER INFORMATION: /= "V28degr2"

(xi) SEQUENCE DESCRIPTION: SEQ ID NO: 6:

GCTAAGCTTT TRTAGGGDGT CCAYAAGAGY AA                          32

(2) INFORMATION FOR SEQ ID NO: 7:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: misc_feature
         (D) OTHER INFORMATION: /= "88c-r4"

(xi) SEQUENCE DESCRIPTION: SEQ ID NO: 7:

GATAAGCCTC ACAGCCCTGT G                                      21

(2) INFORMATION FOR SEQ ID NO: 8:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: misc_feature
         (D) OTHER INFORMATION: /= "88c-r1b"

(xi) SEQUENCE DESCRIPTION: SEQ ID NO: 8:

GCTAAGCTTG ATGACTATCT TTAATGTC                               28

(2) INFORMATION FOR SEQ ID NO: 9:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: misc_feature
         (D) OTHER INFORMATION: /= "88-2B-3"
```

```
        (xi) SEQUENCE DESCRIPTION: SEQ ID NO: 9:

CCCTCTAGAC TAAAACACAA TAGAGAG                                               27

(2) INFORMATION FOR SEQ ID NO: 10:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (D) OTHER INFORMATION: /= "88-2B-5"

(xi) SEQUENCE DESCRIPTION: SEQ ID NO: 10:

GCTAAGCTTA TCACAGGGAG AAGTGAAATG                                            30

(2) INFORMATION FOR SEQ ID NO: 11:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (D) OTHER INFORMATION: /= "88-2B-f1"

(xi) SEQUENCE DESCRIPTION: SEQ ID NO: 11:

AGTGCTAGCA GCTCTTCCTG                                                       20

(2) INFORMATION FOR SEQ ID NO: 12:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (D) OTHER INFORMATION: /= "88-2B-r1"

(xi) SEQUENCE DESCRIPTION: SEQ ID NO: 12:

CAGCAGCGTT TTGATGATTC                                                       20

(2) INFORMATION FOR SEQ ID NO: 13:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (D) OTHER INFORMATION: /= "88C-f1"

(xi) SEQUENCE DESCRIPTION: SEQ ID NO: 13:

TGTGTTTGCT TTAAAAGCC                                                        19
```

(2) INFORMATION FOR SEQ ID NO: 14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (D) OTHER INFORMATION: /= "88C-r3"

(xi) SEQUENCE DESCRIPTION: SEQ ID NO: 14:

TAAGCCTCAC AGCCCTG                                      17

(2) INFORMATION FOR SEQ ID NO: 15:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (D) OTHER INFORMATION: /= "CCCKR1(2)-5 Primer"

(xi) SEQUENCE DESCRIPTION: SEQ ID NO: 15:

CGTAAGCTTA GAGAAGCCGG GATGGGAA                      28

(2) INFORMATION FOR SEQ ID NO: 16:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (iv) ANTI-SENSE: YES (ix) FEATURE:
        (A) NAME/KEY: misc_feature
        (D) OTHER INFORMATION: /= "CCCKR-3 Primer"

(xi) SEQUENCE DESCRIPTION: SEQ ID NO: 16:

GCCTCTAGAG TCAGAGACCA GCAGA                          25

(2) INFORMATION FOR SEQ ID NO: 17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

GACAAGCTTC ACAGGGTGGA ACAAGATG                      28

(2) INFORMATION FOR SEQ ID NO: 18:

(i) SEQUENCE CHARACTERISTICS:

(A) LENGTH: 27 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 18:

GTCTCTAGAC CACTTGAGTC CGTGTCA    27

(2) INFORMATION FOR SEQ ID NO: 19:

(i) SEQUENCE CHARACTERISTICS:
(A) LENGTH: 1059 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..1056

(xi) SEQUENCE DESCRIPTION: SEQ ID NO: 19:

```
ATG GAC TAT CAA GTG TCA AGT CCA ACC TAT GAC ATC GAT TAT TAT ACA       48
Met Asp Tyr Gln Val Ser Ser Pro Thr Tyr Asp Ile Asp Tyr Tyr Thr
 1               5                  10                  15

TCG GAA CCC TGC CAA AAA ATC AAT GTG AAA CAA ATC GCA GCC CGC CTC       96
Ser Glu Pro Cys Gln Lys Ile Asn Val Lys Gln Ile Ala Ala Arg Leu
             20                  25                  30

CTG CCT CCG CTC TAC TCA CTG GTG TTC ATC TTT GGT TTT GTG GGC AAC      144
Leu Pro Pro Leu Tyr Ser Leu Val Phe Ile Phe Gly Phe Val Gly Asn
         35                  40                  45

ATA CTG GTC GTC CTC ATC CTG ATA AAC TGC AAA AGG CTG AAA AGC ATG      192
Ile Leu Val Val Leu Ile Leu Ile Asn Cys Lys Arg Leu Lys Ser Met
 50                  55                  60

ACT GAC ATC TAC CTG CTC AAC CTG GCC ATC TCT GAC CTG CTT TTC CTT      240
Thr Asp Ile Tyr Leu Leu Asn Leu Ala Ile Ser Asp Leu Leu Phe Leu
 65                  70                  75                  80

CTT ACT GTC CCC TTC TGG GCT CAC TAT GCT GCT GCC CAG TGG GAC TTT      288
Leu Thr Val Pro Phe Trp Ala His Tyr Ala Ala Ala Gln Trp Asp Phe
                 85                  90                  95

GGA AAT ACA ATG TGT CAA CTC TTG ACA GGG CTC TAT TTT ATA GGC TTC      336
Gly Asn Thr Met Cys Gln Leu Leu Thr Gly Leu Tyr Phe Ile Gly Phe
            100                 105                 110

TTC TCT GGA ATC TTC TTC ATC ATC CTC CTG ACA ATC GAT AGG TAC CTG      384
Phe Ser Gly Ile Phe Phe Ile Ile Leu Leu Thr Ile Asp Arg Tyr Leu
        115                 120                 125

GCT ATC GTC CAT GCT GTG TTT GCT TTA AAA GCC AGG ACA GTC ACC TTT      432
Ala Ile Val His Ala Val Phe Ala Leu Lys Ala Arg Thr Val Thr Phe
130                 135                 140

GGG GTG GTG ACA AGT GTG ATC ACT TGG GTG GTG GCT GTG TTT GCC TCT      480
Gly Val Val Thr Ser Val Ile Thr Trp Val Val Ala Val Phe Ala Ser
145                 150                 155                 160

CTC CCA GGA ATC ATC TTT ACC AGA TCT CAG AGA GAA GGT CTT CAT TAC      528
Leu Pro Gly Ile Ile Phe Thr Arg Ser Gln Arg Glu Gly Leu His Tyr
                165                 170                 175

ACC TGC AGC TCT CAT TTT CCA TAC AGT CAG TAT CAA TTC TGG AAG AAT      576
Thr Cys Ser Ser His Phe Pro Tyr Ser Gln Tyr Gln Phe Trp Lys Asn
            180                 185                 190

TTT CAG ACA TTA AAG ATG GTC ATC TTG GGG CTG GTC CTG CCG CTG CTT      624
Phe Gln Thr Leu Lys Met Val Ile Leu Gly Leu Val Leu Pro Leu Leu
        195                 200                 205
```

```
GTC ATG GTC ATC TGC TAC TCG GGA ATC CTG AAA ACT CTG CTT CGG TGT        672
Val Met Val Ile Cys Tyr Ser Gly Ile Leu Lys Thr Leu Leu Arg Cys
    210                 215                 220

CGA AAC GAG AAG AAG AGG CAC AGG GCT GTG AGG CTT ATC TTC ACC ATC        720
Arg Asn Glu Lys Lys Arg His Arg Ala Val Arg Leu Ile Phe Thr Ile
225                 230                 235                 240

ATG ATT GTT TAT TTT CTC TTG TGG GCT CCC TAC AAC ATT GTC CTT CTC        768
Met Ile Val Tyr Phe Leu Leu Trp Ala Pro Tyr Asn Ile Val Leu Leu
                245                 250                 255

CTG AAC ACC TTC CAG GAA TTC TTT GGC CTG AAT AAT TGC AGT AGC TCT        816
Leu Asn Thr Phe Gln Glu Phe Phe Gly Leu Asn Asn Cys Ser Ser Ser
            260                 265                 270

AAC AGG TTG GAC CAA GCC ATG CAG GTG ACA GAG ACT CTT GGG ATG ACA        864
Asn Arg Leu Asp Gln Ala Met Gln Val Thr Glu Thr Leu Gly Met Thr
        275                 280                 285

CAC TGC TGC ATC AAC CCC ATC ATC TAT GCC TTT GTC GGG GAG AAG TTC        912
His Cys Cys Ile Asn Pro Ile Ile Tyr Ala Phe Val Gly Glu Lys Phe
    290                 295                 300

AGA AAC TAC CTC TTA GTC TTC TTC CAA AAG CAC ATT GCC AAA CGC TTC        960
Arg Asn Tyr Leu Leu Val Phe Phe Gln Lys His Ile Ala Lys Arg Phe
305                 310                 315                 320

TGC AAA TGC TGT TCC ATT TTC CAG CAA GAG GCT CCC GAG CGA GCA AGT       1008
Cys Lys Cys Cys Ser Ile Phe Gln Gln Glu Ala Pro Glu Arg Ala Ser
                325                 330                 335

TCA GTT TAC ACC CGA TCC ACT GGG GAG CAG GAA ATA TCT GTG GGC TTG       1056
Ser Val Tyr Thr Arg Ser Thr Gly Glu Gln Glu Ile Ser Val Gly Leu
            340                 345                 350

TGA                                                                    1059
```

(2) INFORMATION FOR SEQ ID NO: 20:

(i) SEQUENCE CHARACTERISTICS:
        (A) LENGTH: 352 amino acids
        (B) TYPE: amino acid
        (D) TOPOLOGY: linear (ii) MOLECULE TYPE: protein (xi) SEQUENCE DESCRIPTION: SEQ ID NO: 20:

```
Met Asp Tyr Gln Val Ser Ser Pro Thr Tyr Asp Ile Asp Tyr Tyr Thr
1               5                   10                  15

Ser Glu Pro Cys Gln Lys Ile Asn Val Lys Gln Ile Ala Ala Arg Leu
                20                  25                  30

Leu Pro Pro Leu Tyr Ser Leu Val Phe Ile Phe Gly Phe Val Gly Asn
            35                  40                  45

Ile Leu Val Val Leu Ile Leu Ile Asn Cys Lys Arg Leu Lys Ser Met
        50                  55                  60

Thr Asp Ile Tyr Leu Leu Asn Leu Ala Ile Ser Asp Leu Leu Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
                100                 105                 110

Phe Ser Gly Ile Phe Phe Ile Ile Leu Leu Thr Ile Asp Arg Tyr Leu
            115                 120                 125

Ala Ile Val His Ala Val Phe Ala Leu Lys Ala Arg Thr Val Thr Phe
        130                 135                 140

Gly Val Val Thr Ser Val Ile Thr Trp Val Val Ala Val Phe Ala Ser
```

-continued

```
145                 150                 155                 160
Leu Pro Gly Ile Ile Phe Thr Arg Ser Gln Arg Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Met Val Ile Leu Gly Leu Val Leu Pro Leu Leu
        195                 200                 205

Val Met Val Ile Cys Tyr Ser Gly Ile Leu Lys Thr Leu Leu Arg Cys
    210                 215                 220

Arg Asn Glu Lys Lys Arg His Arg Ala Val Arg Leu Ile Phe Thr Ile
225                 230                 235                 240

Met Ile Val Tyr Phe Leu Leu Trp Ala Pro Tyr Asn Ile Val Leu Leu
                245                 250                 255

Leu Asn Thr Phe Gln Glu Phe Phe Gly Leu Asn Asn Cys Ser Ser Ser
            260                 265                 270

Asn Arg Leu Asp Gln Ala Met Gln Val Thr Glu Thr Leu Gly Met Thr
        275                 280                 285

His Cys Cys Ile Asn Pro Ile Ile Tyr Ala Phe Val Gly Glu Lys Phe
    290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
            340                 345                 350
```